United States Patent
Warshawsky et al.

(10) Patent No.: US 6,770,640 B1
(45) Date of Patent: Aug. 3, 2004

(54) 1-CARBOXYLMETHYL-2-OXO-AZEPAN DERIVATIVES USEFUL AS SELECTIVE INHIBITORS OF MMP-12

(75) Inventors: Alan M. Warshawsky, Carmel, IN (US); Michael J. Janusz, Oregonia, OH (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 434 days.

(21) Appl. No.: 09/467,292

(22) Filed: Dec. 17, 1999

Related U.S. Application Data

(60) Provisional application No. 60/155,205, filed on Dec. 31, 1998.

(51) Int. Cl.[7] ............... C07D 223/12; C07D 401/00; C07D 405/00; C07D 409/00; A61K 31/55
(52) U.S. Cl. ............... 514/212.03; 514/212.08; 540/524; 540/527
(58) Field of Search ............... 540/524, 527; 514/212.03, 212.08

(56) References Cited

U.S. PATENT DOCUMENTS

| | | | |
|---|---|---|---|
| 5,075,302 A | 12/1991 | Neustadt | 514/211 |
| 5,552,397 A | 9/1996 | Karanewsky et al. | 514/212 |
| 5,654,294 A | 8/1997 | Robl | 514/212 |
| 5,856,476 A | 1/1999 | Robl | 540/527 |

FOREIGN PATENT DOCUMENTS

| | | |
|---|---|---|
| EP | 0726072 | 8/1996 |
| EP | 0599444 | 1/1998 |
| WO | 9812211 | 3/1998 |
| WO | 9935145 | 7/1999 |

OTHER PUBLICATIONS

Robl et al., *J. Med. Chem.*, 39,494–502 (1996).
Warshawsky et al., *Bioorg. Med. Chem. Lett.*, 6(8), 957–962 (1996).
Robl et al., *Tetrahedron Lett.*, 37(50), 8985–8988 (1996).
Robl et al., *J. Am. Chem. Soc.*, 116, 2348–2355, 1994.
Robl et al, *Tetrahedron Lett.*, 35(9), 1393–1396,1994.

*Primary Examiner*—Bruck Kifle
(74) *Attorney, Agent, or Firm*—Julie Anne Knight; Raymond S. Parker, III

(57) ABSTRACT

The present invention relates to certain novel 1-carboxymethyl-2-oxo-azepan derivatives of the formula

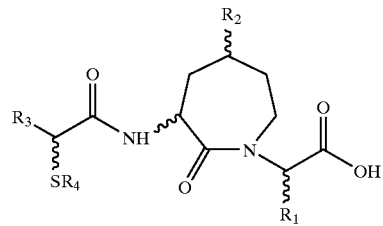

formula (1)

useful as inhibitors of matrix metalloproteinases (MMPs). The compounds of formula (1) are especially useful as selective inhibitors of MMP-12. Pharmaceutical compositions containing said compounds as well as methods of treating various disease states responding to inhibition of matrix metalloproteinase are also claimed herein.

14 Claims, No Drawings

1-CARBOXYLMETHYL-2-OXO-AZEPAN DERIVATIVES USEFUL AS SELECTIVE INHIBITORS OF MMP-12

This application claims the benefit of U.S. Provisional Application No. 60/155,205, filed Dec. 31, 1998.

BACKGROUND OF THE INVENTION

The matrix metalloproteinases (MMP's) are a family of zinc containing endopeptidases which are capable of cleaving large biomolecules such as the collagens, proteoglycans and gelatins. Expression is upregulated by pro-inflammatory cytokines and/or growth factors. The MMP's are secreted as inactive zymogens which, upon activation, are subject to control by endogenous inhibitors, for example, tissue inhibitor of metalloproteinases (TIMP) and $\alpha_2$-macroglobulin. Chapman, K. T. et al., *J. Med. Chem.* 36, 4293–4301 (1993); Beckett, R. P. et al., *DDT* 1, 16–26 (1996). The characterizing feature of diseases involving the enzymes appears to be a stoichiometric imbalance between active enzymes and endogenous inhibitors, leading to excessive tissue disruption, and often degradation. McCachren, S. S., *Arthritis Rheum.* 34, 1085–1093 (1991).

The discovery of different families of matrix metalloproteinase, their relationships, and their individual characteristics have been categorized in several reports. Emonard, H. et al., *Cell Molec. Biol.* 36, 131–153 (1990); Birkedal-Hansen, H., *J. Oral Pathol.* 17, 445–451 (1988); Matrisian, L. M., *Trends Genet.* 6, 121–125 (1990); Murphy, G. J. P. et al., *FEBS Lett.* 289, 4–7 (1991); Matrisian, L. M., *Bioessays* 14, 455–463 (1992). Three groups of MMPs have been delineated: the collagenases which have triple helical interstitial collagen as a substrate, the gelatinases which are proteinases of denatured collagen and Type IV collagen, and the stromelysins which were originally characterized as proteoglycanases but have now been identified to have a broader proteolytic spectrum. Examples of specific collagenases include fibroblast collagenase characterized as proteoglycanases but have now been identified to have a broader proteolytic spectrum. Examples of specific collagenases include fibroblast collagenase (MMP-1), neutrophil collagenase (MMP-8), and collagenase 3 (MMP-13). Examples of gelatinases include 72 kDa gelatinase (gelatinase A; MMP-2) and 92 kDa gelatinase (gelatinase B; MMP-9). Examples of stromelysins include stromelysin 1 (MMP-3), stromelysin 2 (MMP-10) and matrilysin (MMP-7). Other MMPs which do not fit neatly into the above groups include metalloelastase (MMP-12), membrane-type MMP (MT-MMP or MMP-14) and stromelysin 3 (MMP-11). Beckett, R. P. et al., supra.

Over-expression and activation of MMPs have been linked with a wide range of diseases such as cancer; rheumatoid arthritis; osteoarthritis; chronic inflammatory disorders, such as emphysema; cardiovascular disorders, such as atherosclerosis; corneal ulceration; dental diseases such as gingivitis and periodontal disease; neurological disorders, such as multiple sclerosis; and smoking-induced emphysema.

For example, in adenocarcinoma, invasive proximal gastric cells express the 72 kDa form of collagenase Type IV, whereas the noninvasive cells do not. Schwartz, G. K. et al., *Cancer* 73, 22–27 (1994). Rat embryo cells transformed by the Ha-ras and v-myc oncogenes or by Ha-ras alone are metastatic in nude mice and release the 92 kDa gelatinase/collagenase (MMP-9). Bernhard, E. J. et al., *Proc. Natl. Acad. Sci.* 91, 4293–4597 (1994). The plasma concentration of MMP-9 was significantly increased (P<0.01) in 122 patients with gastrointestinal tract cancer and breast cancer. Zucker, S. et al., *Cancer Res.* 53, 140–146 (1993). Moreover, intraperitoneal administration of batimastat, a synthetic MMP inhibitor, gave significant inhibition in the growth and metastatic spread and number of lung colonies which were produced by intravenous injection of the B16-BL6 murine melanoma in C57BL/6N mice. Chirivi, R. G. S. et al., *Int. J. Cancer* 58, 460–464 (1994). Over-expression of TIMP-2, the endogenous tissue inhibitor of MMP-2, markedly reduced melanoma growth in the skin of immunodeficient mice. Montgomery, A. M. P. et al., *Cancer Res.* 54, 5467–5473 (1994).

Accelerated breakdown of the extracellular matrix of articular cartilage is a key feature in the pathology of both rheumatoid arthritis and osteoarthritis. Current evidence suggests that the inappropriate synthesis of MMPs is the key event. Beeley, N. R. A. et al., *Curr. Opin. Ther. Patents*, 4(1), 7–16 (1994). The advent of reliable diagnostic tools have allowed a number of research groups to recognize that stromelysin is a key enzyme in both arthritis and joint trauma. Beeley, N. R. A. et al., Id.; Hasty, K. A. et al., *Arthr. Rheum.* 33, 388–397 (1990). It has also been shown that stromelysin is important for the conversion of procollagenase to active collagenase. Murphy, G. et al., *Biochem. J.* 248, 265–268 (1987).

Furthermore, a range of MMPs can hydrolyse the membrane-bound precursor of the pro-inflammatory cytokine tumor necrosis factor $\alpha$ (TNF-$\alpha$). Gearing, A. J. H. et al., *Nature* 370, 555–557 (1994). This cleavage yields mature soluble TNF-$\alpha$ and the inhibitors of MMPs can block production of TNF-$\alpha$ both in vitro and in vivo. Gearing, A. J. H. et al., Id.; Mohler, K. M. et al., *Nature* 370, 218–220 (1994); McGeehan, G. M. et al., *Nature* 370, 558–561 (1994). This pharmacological action is a probable contributor to the antiarthritic action of this class of compounds seen in animal models. Beckett, R. P. et al., supra.

Stromelysin has been observed to degrade the $\alpha_1$-proteinase inhibitor which regulates the activity of enzymes such as elastase, excesses of which have been linked to chronic inflammatory disorders such as emphysema and chronic bronchitis. Inhibition of the appropriate MMP may thus potentiate the inhibitory activity of endogenous inhibitors of this type. Beeley, N. R. A. et al., supra.; Wahl, R. C. et al., *Annual Reports in Medicinal Chemistry* 25, 177–184 (1990).

High levels of mRNA corresponding to stromelysin have been observed in atherosclerotic plaques removed from heart transplant patients. Henney, A. M., et al., *Proc. Natl. Acad. Sci.* 88, 8154–8158 (1991). It is submitted that the role of stromelysin in such plaques is to encourage rupture of the connective tissue matrix which encloses the plaque. This rupture is in turn thought to be a key event in the cascade which leads to clot formation of the type seen in coronary thrombosis. MMP inhibition is thus a preventive measure for such thromboses.

Collagenase, stromelysin and gelatinase have been implicated in the destruction of the extracellular matrix of the cornea. This is thought to be an important mechanism of morbidity and visual loss in a number of ulcerative ocular diseases, particularly those following infection or chemical damage. Burns, F. R. et al., *Invest. Opthalmol. and Visual Sci.* 32, 1569–1575 (1989). The MMPs present in the eye during ulceration are derived either endogenously from infiltrating leucocytes or fibroblasts, or exogenously from microbes.

Collagenase and stromelysin activities have been identified in fibroblasts isolated from inflamed gingiva and the levels of enzyme have been correlated with the severity of the gingivitis observed. Beeley, N. R. A. et al., supra.; Overall, C. M. et al., *J. Periodontal Res.* 22, 81–88 (1987).

Excessive levels of gelatinase-B in cerebrospinal fluid has been linked with incidence of multiple sclerosis and other neurological disorders. Beeley, N. R. A. et al., supra.; Miyazaki, K. et al., *Nature* 362, 839–841 (1993). The enzyme may play a key role in the demyelination of neurones and the breakdown of the blood brain barrier which occurs in such disorders.

In addition, a recent study indicates that MMP-12 is required for the development of cigarette smoke-induced emphysema in mice. Science, 277, 2002 (1997).

Apart from the role of these potentially very destructive enzymes in pathology, the MMPs play an essential role in cell regrowth and turnover in healthy tissue. Broad spectrum inhibition of the MMPs in the clinical setting results in musculoskeletal stiffness and pain. H. S. Rasmussen and P. P. McCann, *Pharmacol. Ther.*, 75, 69–75 (1997). This side effect and others associated with broad spectrum inhibition may be enhanced in chronic administration. Thus, it would be advantageous to provide selective MMP inhibitors.

While the 1-carboxymethyl-2-oxo-azepan derivatives of the present application are useful for inhibition of MMP-1, MMP-2, and MMP-3 they are selective inhibitors of MMP-12. Because they are selective, the compounds of the present application are expect to be useful for long term therapy with less of the complications related to broad spectrum inhibition. Thus, while the compounds of the present application are useful for the treatment of a variety of MMP mediated diseases and conditions, these selective inhibitors are particularly useful for the treatment of smoking-induced emphysema.

SUMMARY OF THE INVENTION

The present invention provides novel compounds of the formula

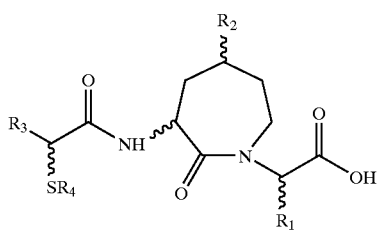

formula (1)

wherein
$R_1$ is selected from a group consisting of hydrogen, $C_1$–$C_6$ alkyl, —$CH_2SCH_2NHCOCH_3$, —$(CH_2)_p$—A, —$(CH_2)_m$—B, and —$CH_2$—D—$R_7$;
wherein
A is selected from a group consisting of $C_6$–$C_{10}$ aryl, $C_3$–$C_9$ heteroaryl, or cyclohexyl;
B is selected from a group consisting of —$N(R_7)_2$, guanidino, nitroguanidino, —C(O)O$R_6$ and —C(O)N$R_6$;
D is selected from a group consisting of oxy and thio;
$R_2$ is selected from a group consisting of $C_1$–$C_4$ alkyl, —$(CH_2)_p$—$(C_3$–$C_9)$ heteroaryl, and —$(CH_2)_p$—$Ar_1$;
wherein
$Ar_1$ is selected from the group consisting of phenyl and naphthyl optionally substituted with a substituent selected from the group consisting of halogen, $C_1$–$C_4$ alkyl, —O$R_6$, —N$(R_6)_2$, —$SO_2N(R_6)_2$ and —$NO_2$;
$R_3$ is selected from a group consisting of $C_1$–$C_6$ alkyl, W—$(CH_2)_m$—, and Q—Z—$(CH_2)_m$—;
wherein
W is phthalimido;
Z is selected from the group consisting of a bond, —O—, —N$R_6$—, —C(O)N$R_6$—, —N$R_6$C(O)—, —NHC(O)N$R_6$—, —OC(O)N$R_6$—, —HNC(O)O—, and —$SO_2NR_6$—;
Q is selected from the group consisting of hydrogen, and Y—$(CH_2)_n$—;
wherein
Y is selected from the group consisting of hydrogen, $C_6$–$C_{10}$ aryl, $C_3$–$C_9$ heteroaryl, —C(O)O$R_6$, —N$(R_6)_2$, morpholino, piperidino, pyrrolidino, and isoindolyl;
$R_4$ is selected from a group consisting of hydrogen, —C(O)$R_7$, —C(O)—$(CH_2)_q$—K and —S—G;
wherein
K is selected from the group consisting of

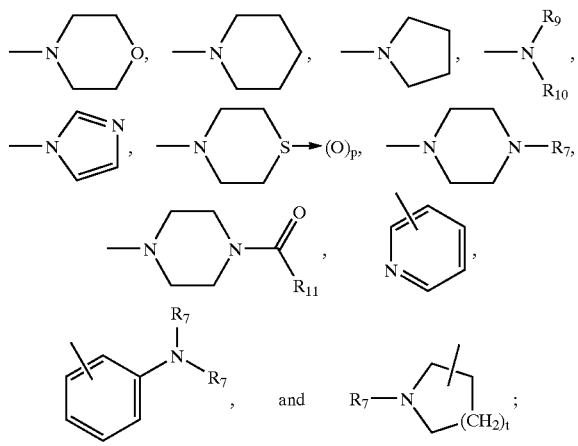

G is selected from the group consisting of $R_6$ is selected from the group consisting of hydrogen and $C_1$–$C_6$ alkyl;
$R_7$ is selected from the group consisting of hydrogen, $C_1$–$C_4$ alkyl, and —$(CH_2)_p$—$Ar_2$;
wherein Ar$_2$ is selected from the group consisting of phenyl and naphthyl optionally substituted with a substituent selected from the group consisting of halogen, C$_1$–C$_4$ alkyl, —OR$_6$, —N(R$_6$)$_2$, —SO$_2$N(R$_6$)$_2$ and —NO$_2$;

R$_9$ and R$_{10}$ are each independently selected from the group consisting of C$_1$–C$_4$ alkyl and —(CH$_2$)$_p$—Ar$_2$;

R$_{11}$ is selected from the group consisting of —CF$_3$, C$_1$–C$_{10}$ alkyl and —(CH$_2$)$_p$—Ar$_2$;

R$_{12}$ is selected from the group consisting of hydrogen, C$_1$–C$_6$ alkyl, —CH$_2$CH$_2$S(O)$_p$CH$_3$, and arylalkyl;

R$_{13}$ is selected from the group consisting of hydrogen, hydroxy, amino, C$_1$–C$_6$ alkyl, N-methylamino, N,N-dimethylamino, —CO$_2$R$_{17}$ and —OC(O)R$_{18}$; wherein R$_{17}$ is selected from the group consisting of hydrogen, —C(O)C(CH$_3$)$_3$, C$_1$–C$_4$ alkyl, —(CH$_2$)$_p$—Ar$_2$, and diphenylmethyl;

R$_{18}$ is hydrogen, C$_1$–C$_6$ alkyl and phenyl;

R$_{14}$ is selected from the group consisting of 1 or 2 substituents independently chosen from the group consisting of hydrogen, C$_1$–C$_4$ alkyl, C$_1$–C$_4$ alkoxy, and halogen;

R$_{15}$ is selected from the group consisting of hydrogen, C$_1$–C$_6$ alkyl and —(CH$_2$)$_p$—Ar$_2$;

R$_{16}$ is selected from the group consisting of hydrogen and C$_1$–C$_4$ alkyl;

V$_1$ is selected from the group consisting of —O—, —S—, and —NH—;

V$_2$ is selected from the group consisting of —N— and —CH—;

V$_3$ is selected from the group consisting of a bond and —C(O)—;

V$_4$ is selected from the group consisting of —(CH$_2$)$_w$—, —O—, —S—, —NR$_7$—, and —NC(O)R$_{11}$—;

X' is selected from the group consisting of —CH— and —N—;

m is an integer from 2–4;
n is an integer from 0–4;
p is an integer from 0–2;
t is an integer from 1–2;
w is an integer from 1–3;
w' is an integer from 0–1;

or a pharmaceutically acceptable salt, stereoisomer or hydrate thereof.

The present invention further provides a method of inhibiting matrix metallo-proteinases (MMPS) in a patient in need thereof comprising administering to the patient an effective matrix metalloproteinase inhibiting amount of a compound of formnula (1).

In addition, the present invention provides a composition comprising an assayable amount of a compound of formula (1) in admixture or otherwise in association with an inert carrier. The present invention also provides a pharmaceutical composition comprising an effective MMP inhibitory amount of a compound of formula (1) in admixture or otherwise in association with one or more pharmaceutically acceptable carriers or excipients.

DETAILED DESCRIPTION OF THE PREFERRED EMBODIMENTS

As used in this application:

a) the designation "Aly*        " refers to a bond for which the stereochemistry is not designated.

b) the designation "Aly*        " refers to a bond that protrudes forward out of the plane of the page.

c) the designation "Aly*        " refers to a bond that protrudes backward out of the plane of the page.

d) the term "C$_1$–C$_4$ alkyl" refers to a saturated straight or branched chain hydrocarbyl radical of one to four carbon atoms and includes methyl, ethyl, propyl, isopropyl, n-butyl, isobutyl, tertiary butyl and the like.

e) the term "C$_1$–C$_6$ alkyl" refers to a saturated straight or branched chain hydrocarbyl radical of one to six carbon atoms and includes methyl, ethyl, propyl, isopropyl, n-butyl, isobutyl, tertiary butyl, n-pentyl, sec-pentyl, isopentyl, n-hexyl and the like.

f) the term "C$_1$–C$_{10}$ alkyl" refers to a saturated straight or branched chain hydrocarbyl radical of one to ten carbon atoms and includes methyl, ethyl, propyl, isopropyl, n-butyl, isobutyl, tertiary butyl, n-pentyl, sec-pentyl, isopentyl, n-hexyl, 2,3-dimethyl-2-butyl, heptyl, 2,2-dimethyl-3-pentyl, 2-methyl-2-hexyl, octyl, 4-methyl-3-heptyl, nonyl, decyl and the like.

g) the term "C$_1$–C$_4$ alkoxy" refers to a straight or branched alkoxy group containing from 1 to 4 carbon atoms, such as methoxy, ethoxy, n-propoxy, isopropoxy, n-butoxy, isobutoxy, t-butoxy, and the like.

h) the designation "—C(O)—" refers to a carbonyl group of the formula

i) the term "C$_6$–C$_{10}$ aryl" refers to a cyclic aromatic assemblage of conjugated carbon atoms, optionally substituted with one to three substituents selected from the group consisting of F, Cl, C$_1$–C$_4$ alkyl, —OR$_7$, —N(R$_6$)$_2$, or —NO$_2$, including phenyl, 1-naphthyl, 2-naphthyl, 2-hydroxyphenyl, 3-hydroxyphenyl, 4-hyroxyphenyl, 2,3-dihydroxyphenyl, 2,4-dihydroxyphenyl, 3,4-dihydroxyphenyl, 2,3,4-trihydroxyphenyl, 4-methoxyphenyl, 4-ethoxyphenyl, 2-chlorophenyl, 3-chlorophenyl, 4-chlorophenyl, 3,4-dichlorophenyl, 2,3,4-trichlorophenyl, 4-bromophenyl, 3,4-dibromophenyl, 4-fluorophenyl, 3,4-difluorophenyl, 3-tolyl, 4-tolyl, 4-ethylphenyl, 4-isopropylphenyl, 3-aminophenyl, 4-aminophenyl, 3,4-diaminophenyl, N-methyl-4-aminophenyl, 2-nitrophenyl, 4-nitrophenyl, 3-bromo-4-tolyl, and the like.

j) the term "C$_3$–C$_9$ heteroaryl" means a cyclic or bicyclic, aromatic assemblage of conjugated carbon atoms and from 1 to 3 nitrogen, oxygen and sulfur atoms, for example, pyridinyl, 2-quinoxalinyl, quinolinyl, pyridazinyl, pyrimidyl, pyrazolyl, pyrazyl, thiophyl, furyl, imidazolyl, oxazolyl, thiazolyl, benzimidazolyl and the like.

k) the terms "PhtN" or "phthalimido" refer to a phthalimido (1,3-dihydro-1,3-dioxo-(2H)—isoindolyl) functionality of the formula:

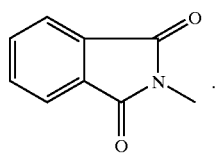

l) the designations "C(O)NR$_6$", "NR$_6$C(O)", "NHC(O)NR$_6$", "OC(O)NR$_6$", "R$_6$NC(O)O" or "SO$_2$NR$_6$" refer to amide bond or modified amide bond functionalities and are represented, respectively, by the following formulae:

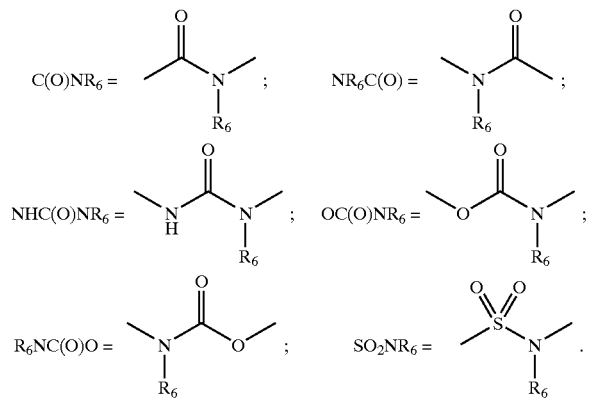

m) the terms "Ar$_1$", "Ar$_2$" or "aryl" refers to a phenyl or naphthyl group unsubstituted or substituted with from one to three substituents selected from the group consisting of F, Cl, C$_1$-C$_4$ alkyl, —OR$_7$, —N(R$_6$)$_2$, SO$_2$N(R$_6$)$_2$ or —NO$_2$; specifically included within the scope of the term "aralkyl" are phenyl, naphthyl, naphthylmethyl, phenylmethyl or benzyl, phenylethyl, p-methoxybenzyl, 3,4-methylenedioxybenzyl, p-fluorobenzyl and p-chlorobenzyl.

For the purposes of this invention, when "Ar$_1$" is phenyl, shown below,

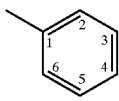

the radical is attached in the 1-position and the substituent or substituents may only be attached at the 3, 4 or 5 positions of the phenyl moiety.

When "Ar$_1$" is naphthyl, shown below,

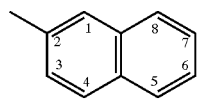

the radical can be attached at the 2-position, and the substituent or substituents may only be attached at the 5, 6, 7 or 8 positions.

For the purposes of this invention, when "Ar$_2$" is phenyl, the substituent or substituents can be attached at the 2, 3, 4, 5 or 6 positions of the phenyl moiety. When "Ar$_2$" isnaphthyl, it is understood that the radical can be attached at the either the 1-position or the 2-position, it is further understood that when the radical is attached at the 1-position the substituent or substituents can be attached in any of the 2, 3, 4, 5, 6, 7, or 8 positions and that when the radical is attached at the 2-position the substituent or substituents can be attached in any of the 1, 3, 4, 5, 6, 7, or 8 positions.

n) the term "halogen" refers to fluorine, chlorine, bromine or iodine.

o) the term "pharmaceutically acceptable salts" thereof refers to either an acid addition salt or a basic addition salt.

The expression "pharmaceutically acceptable acid addition salts" is intended to apply to any non-toxic organic or inorganic acid addition salt of the base compounds represented by formula (1) or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid, and sulfonic acids such as methane sulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The expression "pharmaceutically acceptable basic addition salts" is intended to apply to any non-toxic organic or inorganic basic addition salts of the compounds represented by formula (1) or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline.

The term "stereoisomers" is a general term for all isomers of individual molecules that differ only in the orientation of their atoms in space. It includes mirror image isomers (enantiomers), geometric (cis/trans) isomers, and isomers of compounds with more than one chiral center that are not mirror images of one another (diastereomers). Any reference in this application to one of the compounds of formula (1) is meant to encompass either specific stereoisomers or a mixture of stereoisomers. The specific stereoisomers can be prepared by stereospecific synthesis or can be separated and recovered by techniques known in the art, such as chromatography, chromatography on chiral stationary phases, fractional recrystallization of addition salts formed by reagents used for that purpose, as described in *Stereochemistry of Organic Compounds*, E. L. Eliel and S. H. Wilen, Wiley (1994) and *Enantiomers, Racemates, and Resolutions*, J. Jacques, A. Collet, and S. H. Wilen, Wiley (1981).

As with any group of structurally related compounds which possess a particular utility, certain groups and configurations of substituents are preferred for the compounds of formula (1). Preferred embodiments are given below:

1) A preferred embodiment of the novel compounds is that of formula (1) are compounds in which R$_3$ is C$_1$-C$_6$ alkyl.

2) A preferred embodiment of the novel compounds is that of formula (1) are compounds in which R$_3$ is a Q—Z—(CH$_2$)$_m$— group.

3) A preferred embodiment of the novel compounds is that of formula (1) are compounds in which R$_2$ is a —(CH$_2$)$_p$—Ar$_1$ group wherein Ar$_1$ is phenyl optionally substituted with F, Cl, C$_1$-C$_4$ alkyl, or —OR$_7$.

4) A preferred embodiment of the novel compounds is that of formula (1) are compounds in which $R_1$ is a a —($CH_2$)$_p$—A group, wherein A is $C_6$–$C_{10}$ aryl.

5) A preferred embodiment of the novel compounds is that of formula (1) are compounds in which $R_3$ is a W—($CH_2$)$_m$— group.

6) A preferred embodiment of the novel compounds is that of formula (1) are compounds in which $R_4$ is hydrogen.

7) A preferred embodiment of the novel compounds is that of formula (1) are compounds in which $R_4$ is —C(O)$R_7$.

8) A preferred embodiment of the novel compounds is that of formula (1) are compounds in which $R_4$ is a —S—G group.

9) A more preferred embodiment of the novel compounds is that of formula (1) are compounds in which $R_1$ is a a —($CH_2$)$_p$—A group, wherein A is phenyl or optionally substituted phenyl.

10) A more preferred embodiment of the novel compounds is that of formula (1) are compounds in which $R_3$ is $C_1$–$C_6$ alkyl, preferably methyl, ethyl, propyl, isopropyl, butyl or isobutyl; $R_2$ is —($CH_2$)$_p$—$Ar_1$ group wherein p is 0 and $Ar_1$ is phenyl optionally substituted with F, Cl, $C_1$–$C_4$ alkyl, or —OR$_7$; and $R_4$ is hydrogen, —C(O)$R_7$, or a —S—G group.

11) A more preferred embodiment of the novel compounds is that of formula (1) are compounds in which $R_3$ is a W—($CH_2$)$_m$— group; $R_2$ is —($CH_2$)$_p$—$Ar_1$ group wherein p is 0 and $Ar_1$ is phenyl optionally substituted with F, Cl, $C_1$–$C_4$ alkyl, or —OR$_7$; and $R_4$ is hydrogen, —C(O)$R_7$, or a —S—G group.

Examples of compounds encompassed by the present invention include the following. It is understood that the examples encompass all of the isomers of the compound and mixtures thereof. This list is meant to be representative only and is not intended to limit the scope of the invention in any way:

N-[Hexahydro-1-[1-(phenylethyl)-1-carboxymethyl]-2-oxo-5-phenyl-1H-azepin-3-yl]-1,3-dihydro-α-mercapto-1,3-dioxo-2H-isoindole-2-hexanamide;

N-[Hexahydro-1-[1-(phenylmethyl)-1-carboxymethyl]-2-oxo-5-phenyl-1H-azepin-3-yl]-α-mercapto-3-phenylpropionamide;

N-[Hexahydro-1-[1-(phenylmethyl)-1-carboxymethyl]-2-oxo-5-phenyl-1H-azepin-3-yl]-α-mercapto-4-methylbutamide;

N-[Hexahydro-1-[1-(phenylmethyl)-1-carboxymethyl]-2-oxo-5-phenyl-1H-azepin-3-yl]-1,3-dihydro-α-mercapto-1,3-dioxo-2H-isoindole-2-pentamide;

N-[Hexahydro-1-[1-(phenylmethyl)-1-carboxymethyl]-2-oxo-5-phenyl-1H-azepin-3-yl]-1,3-dihydro-α-mercapto-1,3-dioxo-2H-isoindole-2-heptaamide;

N-[Hexahydro-1-[1-(phenylmethyl)-1-carboxymethyl]-2-oxo-5-phenyl-1H-azepin-3-yl]-1,3-dihydro-α-acetylthio-1,3-dioxo-2H-isoindole-2-hexanamide;

N-[Hexahydro-1-[1-(phenylmethyl)-1-carboxymethyl]-2-oxo-5-phenyl-1H-azepin-3-yl]-1,3-dihydro-α-benzoylthio-1,3-dioxo-2H-isoindole-2-hexanamide;

N-[Hexahydro-1-[1-(phenylmethyl)-1-carboxymethyl]-2-oxo-5-phenyl-1H-azepin-3-yl]-1,3-dihydro-α-ethyldithio-1,3-dioxo-2H-isoindole-2-hexanamide; and N-[Hexahydro-1-[1-(phenylmethyl)-1-carboxymethyl]-2-oxo-5-phenyl-1H-azepin-3-yl]-1,3-dihydro-α-(2-hydroxyethyl)dithio-1,3-dioxo-2H-isoindole-2-hexanamide.

The compounds of formula (1) can be prepared by utilizing techniques and procedures well known and appreciated by one of ordinary skill in the art. A general synthetic scheme for preparing these compounds is set forth in Scheme A wherein all substituents are as previously defined unless otherwise indicated.

SCHEME A

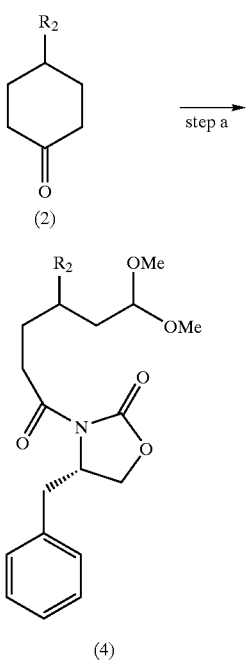

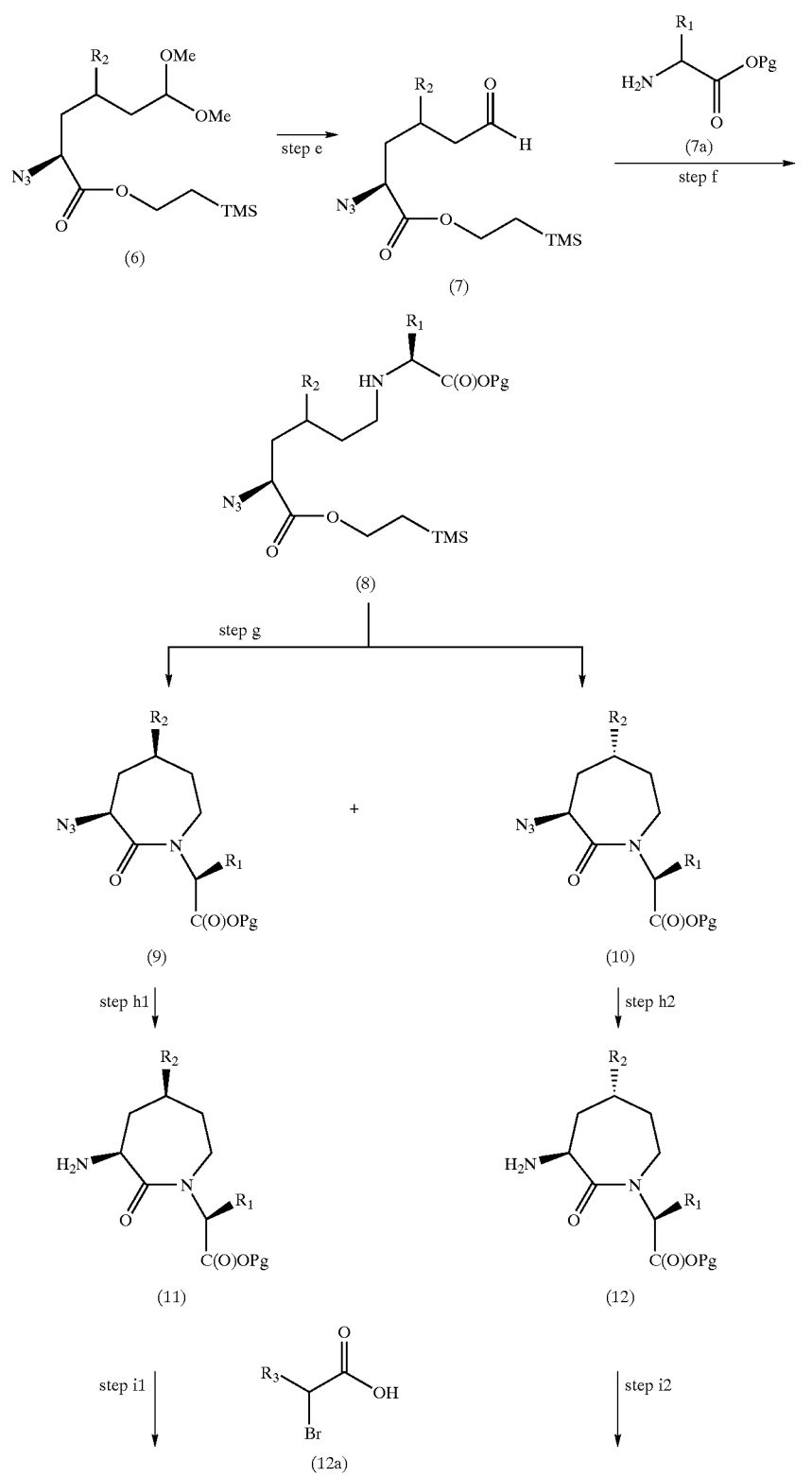
-continued

-continued
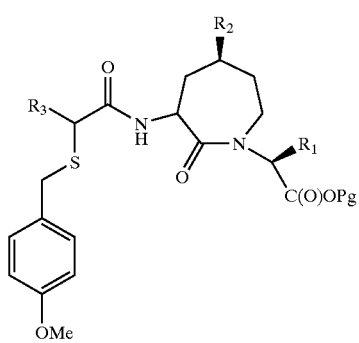
(13)
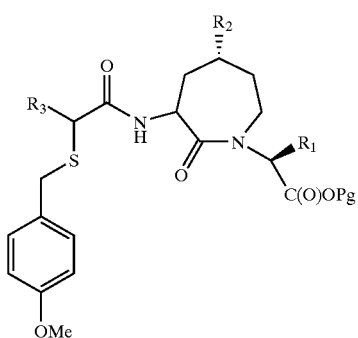
(14)
step j1 ↓   step j2 ↓
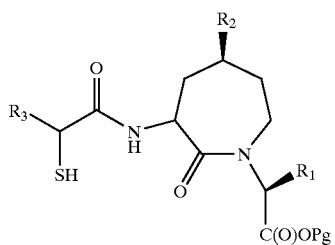
(15)
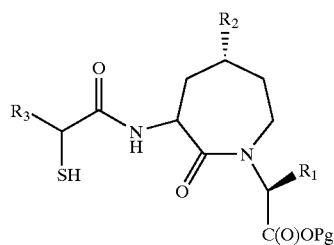
(16)
step k1 ↓   step k2 ↓
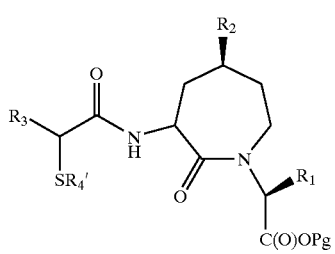
(17)
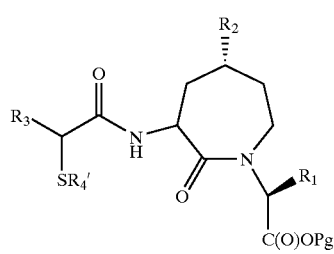
(18)
optional step l1 ↓   optional step l2 ↓
(17a)   (18a)
step m ↓   step m ↓

-continued

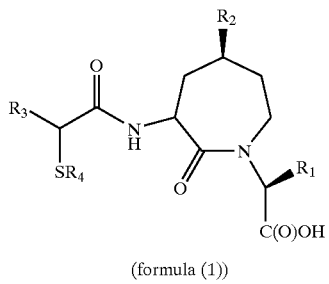

(formula (1))

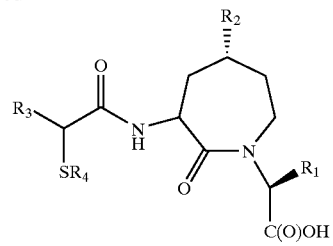

(formula (1))

Scheme A provides a general synthetic procedure for preparing compounds of formula (1). The substituents $R_1$, $R_2$, $R_3$, and $R_4$ are defined as above, while the substituent $R_4'$ is defined as —C(O)R$_7$.

In Scheme A, step a, the appropriate $R_2$-substituted cyclohexanone of structure (2) is enolized with a non-nucleophilic base and quenched with a suitable electrophile, such as chlorotrimethylsilane, to form the corresponding $R_2$-substituted enol ether, followed by treatment with ozone, dimethylsulfide, trimethylortho-formate and a suitable base to provide the appropriate $R_2$-substituted acid of structure (3). $R_2$-substituted cyclohexanones of structure (2) are commercially available, known in the art, or can be prepared as described herein.

For example, lithium diisopropylamide (LDA) is generated by the addition of n-butyllithium to di-isopropylamine in the presence of a suitable organic solvent such as tetrahydrofuran (THF). A solution of $R_2$-substituted cyclohexanone of structure (2) in a suitable organic solvent, such as tetrahydrofuran, is then added at −78° C. After a period of time ranging from about 1 to 3 hours, the reaction is quenched with chloromethylsilane and the mixture is stirred followed by extraction and concentration of the organic layer to yield the silyl enol ether intermediate.

The silyl enol ether intermediate is then dissolved in a suitable organic solvent or solvent mixture, such as a methylene chloride/methanol mixture, cooled to −78° C. and treated with ozone. Dimethyl sulfide is added and the reaction mixture is allowed to warm gradually to ambient temperature over a period of time ranging from 10 to 20 hours. The solution is then concentrated and treated with an orthoformate reagent such as trimethylorthoformate and an acid source such as acetyl chloride and heated to reflux. After a period of time ranging from 4 to 6 hours, the mixture is cooled to ambient temperature and treated with a suitable base, such as potassium hydroxide. The appropriate $R_2$-substituted acid of structure (3) can be isolated by methods well known and appreciated in the art, such as extraction and evaporation.

In Scheme A, step b, the appropriate $R_2$-substituted acid of structure (3) is reacted with lithiated (S)-4-benzyl-2-oxazolidinone to provide the appropriate acyloxazolidinone of structure (4). As depicted in Scheme A, the use of (S)-4-benzyl-2-oxazolidinone in Scheme A gives rise to a 3-aminoazepan having the (S)-configuration at the 3-position. As is appreciated by those skilled in the art, the use of (R)-4-benzyl-2-oxazolidinone would give a 3-aminoazepan having the opposite configuration if desired in the final product of formula (1).

For example, the appropriate $R_2$-substituted acid of structure (3) in a suitable organic solvent, such as tetrahydrofuran, is treated with a suitable tertiary organic amine such as triethylamine or N-methylmorpholine and cooled to −78° C. A suitable acid halide such as trimethylacetyl chloride is added and the mixture is transferred to an ice bath for 0.5 to 1.0 hours, then recooled to −78° C. The resulting slurry is treated with lithiated (S)-4-benzyl-2-oxazolidinone, prepared by adding n-butyllithium to (S)-4-benzyl-2-oxazolidinone in tetrahydrofuran, and allowed to warm gradually to ambient temperature over a period of time ranging from about 10 to 20 hours. The appropriate acyloxazolidinone of structure (4) can be isolated by methods well known and appreciated in the art, such as extraction and evaporation. The product can be purified by methods well known and appreciated in the art, such as flash chromatography.

In Scheme A, step c, the appropriate acyloxazolidinone of structure (4) undergoes an azide introduction reaction with a suitable azide transfer agent to provide the appropriate α-azidoacyloxazolidinone of structure (5).

For example, a solution of a suitable amide such as potassium bis(trimethylsilyl)amide in a suitable organic solvent, such as tetrahydrofuran, is cooled to −78° C. and treated with a solution of the appropriate acyloxazolidinone of structure (4) in tetrahydrofuran, precooled to −78° C. A solution of a suitable azide transfer agent, such as triisopropylbenzenesulfonyl azide, in a suitable organic solvent, such as tetrahydrofuran, precooled to −78° C. is then added. The solution is stirred, quenched with acetic acid and transferred to an oil bath having a temperature of from about 25–40° C. After a period of time ranging from about 1 to 2 hours, the suspension is cooled to ambient temperature and water is added to obtain a solution. The appropriate α-azidoacyloxazolidinone of structure (5) can be isolated by methods well known and appreciated in the art, such as extraction and evaporation. The product can be purified by methods well known in the art, such as flash chromatography.

In Scheme A, step d, the appropriate α-azidoacyloxazolidinone of structure (5) is converted to the corresponding α-azidoacid and then reacted with 2-trimethylsilylethanol to give the corresponding α-azidoester of structure (6). It is understood that protecting groups other than 2-trimthylsilyl may be introduced. The only requirements for this protecting group are that it is stable to the conditons used in Scheme A, steps e and f and that it can be selectively removed in the presence of the protecting group, Pg, introduced in the carboxy protected amino acid (7a). The use and selective removal of carboxy protecting groups is well known and appreciated in the art and described in *Protective Groups in Organic Synthesis*, Theodora W. Greene (Wiley-Interscience, 2nd Edition, 1991).

For example, the appropriate α-azidoacyloxazolidinone of structure (5) in a suitable solvent such as tetrahydrofuran or tetrahydrofuran/water mixtures, is cooled and treated with hydrogen peroxide and a suitable base, such as lithium hydroxide. The mixture is stirred for about 1 to 2 hours and allowed to warm to ambient temperature and treated with sodium sulfite. The corresponding α-azidoacid is isolated by methods well known and appreciated in the art, such as extraction and evaporation.

The corresponding α-azidoacid in a suitable organic solvent, such as tetrahydrofuran, is then treated sequentially at ambient temperature with 2-trimethylsilylethanol, an organic amine, such as pyridine, and a condensing agent such as 1-(3-dimethylaminopropyl)-3-ethylcarbodiimide hydrochloride (EDC). The mixture is then stirred for about 1 to 3 days and then concentrated. The corresponding α-azidoester of structure (6) can be isolated by methods well known and appreciated in the art, such as extraction and evaporation. The product can be purified by methods well known and appreciated in the art, such as flash chromatography.

In Scheme A, step e, the α-azidoester of structure (6) is contacted with a suitable organic acid to provide the corresponding aldehyde-ester of structure (7).

For example, a solution of α-azidoester of structure (6) in the presence of a suitable organic acid, such as acetic acid, and a suitable organic solvent, such as a tetrahydrofuran/water mixture, is heated at a temperature ranging from about 55° C. to about 70° C. for about 3 to 5 hours. The solution is then cooled and the corresponding aldehyde-ester of structure (7) is isolated by methods well known and appreciated in the art, such as extraction and evaporation. The product can be purified by methods well known and appreciated in the art, such as flash chromatography.

In Scheme A, step f, the aldehyde-ester of structure (7) undergoes a reductive, amination with an carboxy protected amino acid of structure (7a), or a salt thereof, to provide the corresponding amino-ester of structure (8). Suitable carboxy protected amino acids, including their specific stereoisomers, are commercially available, are prepared from amino acid starting materials which are commercially available, or can be prepared by stereospecific synthesis as is well known in the art or analogously known in the art, such as D. A. Evans, et al. *J. Am. Chem. Soc.*, 112, 4011–4030 (1990); S. Ikegami et al. *Tetrahedron*, 44, 5333–5342 (1988); W. Oppolzer et al. *Tet. Lets.* 30, 6009–6010 (1989); *Synthesis of Optically Activeα-Amino-Acids*, R. M. Williams (Pergamon Press, Oxford 1989); M. J. O'Donnell ed.: *α-Amino-Acid Synthesis*, Tetrahedron Symposia in print, No. 33, *Tetrahedron* 44, No. 17 (1988); U. Schöllkopf, *Pure Appl. Chem.* 55, 1799 (1983); U. Hengartner et al. *J. Org. Chem.*, 44, 3748–3752 (1979); M. J. O'Donnell et al. Tet. Lets., 2641–2644 (1978); M. J. O'Donnell et al. *Tet. Lets.* 23, 4255–4258 (1982); M. J. O'Donnell et al. *J. Am. Chem. Soc.*, 110, 8520–8525 (1988).

For example, a solution of the aldehyde ester of structure (7) and a carboxy protected amino acid of structure (7a) in a hydroxylic solvent, such as methanol or ethanol, is treated with powdered activated 3 Å sieves. After about 30 minutes to 1 hour, the solution is reacted with a suitable reducing agent such as sodium cyanoborohydride, lithium cyanoborohydride, and the like. The amino-ester of structure (8) is isolated by methods well known and appreciated in the art, such as extraction and evaporation. The product can be purified by methods well known and appreciated in the art, such as flash chromatography.

In Scheme A, step g, the amino-ester of structure (8) is cyclized, after selected carboxy protecting group removal, to give a mixture of the cis α-azidolactam of structure (9) and the trans α-azidolactam of structure (10).

For example, where the 2-trimethylsilyl protecting group is used, a solution of the amino-ester of structure (8) in a suitable organic solvent, such as tetrahydrofuran, is treated at ambient temperature with a fluoride ion source, such as tetra-n-butylammonium fluoride, and stirred. After about 2 to 4 hours, the solution is concentrated. The residue is then dissolved in a suitable organic solvent, such as ethyl acetate, washed with a suitable acid, such as 10% aqueous hydrochloric acid, and brine. The organic layer is then dried and concentrated to yield the corresponding crude amino acid.

The crude amino acid is then dissolved in a suitable organic solvent, such as tetrahydrofuran, cooled in an ice bath and treated sequentially with a suitable tertiary amine, such as N-methylmorpholine, and isobutyl chloroformate. The suspension is stirred for about 2 to 3 hours and filtered. The salts are washed with dry tetrahydrofuran and the filtrate is concentrated. The residue may be purified by methods well known and appreciated in the art, such as radial chromatography, to afford separately, the cis α-azidolactam of structure (9) and the trans α-azidolactam of structure (10).

In Scheme A, steps h1 and h2, the cis α-azidolactam of structure (9) and the trans α-azidolactam of structure (10), respectively, are converted to the corresponding cis α-aminolactam of structure (11) and the trans (α-aminolactam of structure (12), respectively.

For example, a solution of cis α-aminolactam of structure (9) or trans α-azidolactam of structure (10) in a protic solvent, such as methanol or ethanol, is degassed and treated with an alkyl dithiol, such as 1,3-propanedithiol and a tertiary amine, such as triethylamine. The solution is stirred from 60 to 72 hours and then concentrated. The residue may be purified by methods well known and appreciated in the art, such as flash chromatography, to afford the corresponding cis α-aminolactam of structure (11) or the trans α-aminolactam of structure (12), respectively.

In Scheme A, steps i1 and i2, the cis α-aminolactam of structure (11) and the trans α-aminolactam of structure (12), respectively, are coupled with the bromoacid of structure (12a) to provide the bromoamides of structures (13) and (14), respectively. Suitable bromoacids are commercially available or can be prepared utilizing materials, techniques, and procedures well known and appreciated by one of ordinary skill in the art or described herein. See PCT Application WO 96/11209, published 18 Apr. 1996. Examples of commercially available bromoacids include 2-bromopropionic acid, 2-bromobutyric acid, 2-bromovaleric acid, 2-bromohexanoic acid, 6-(benzoylamino)-2-bromohexanoic acid, 2-bromoheptanoic acid, 2-bromooctanoic acid, 2-bromo-3-methylbutyric acid, 2-bromoisocaproic acid, 2-bromo-3-(5-imidazoyl)propionic acid, (R)-(+)-2-bromopropionic acid, (S)-(−)-2-bromopropionic acid.

For example, a mixture of cis α-aminolactam of structure (11) or trans α-aminolactam of structure (12), a bromoacid of structure (12a), a carbodiimide, such as 1-(3-dimethylaminopropyl)-3-ethylcarbodiimide hydrochloride (EDC), and 1-hydroxybenzotriazole (HOBt) in a suitable organic solvent such as methylene chloride was stirred at ambient temperature for 15 to 25 hours. The cis bromoamide of structure (13) or the trans bromoamide of structure (14) may be isolated by methods well known and appreciated in the art, such as extraction and evaporation. The product can be purified by methods well known and appreciated in the art, such as flash chromatography.

In Scheme A, steps j1 and j2, the cis bromoamide of structure (13) and the trans bromoamide of structure (14), respectively, are converted to the cis α-thioamide of structure (15) and the trans α-thioamide of structure (16), respectively. This displacement reaction can be carried out using an appropriate thio introducing reagent to give compound of formula (15) and (16) having a protected thio substituent. Such protected thio substituents give rise upon deprotection and subsequent elaboration, if desired, the —SR$_4$ as desired in the final compound of formula (1). An appropriate thio introducing reagent is also one which introduces a group —SF$_4$ as desired in the final compound of formula (1), such as thioacetyl or thiobenzoyl or the group —SC(O)—(CH$_2$)$_q$—K.

For example, a solution of p-methoxybenzylmercaptan in a suitable organic solvent such as dimethylformamide is degassed and treated with a suitable base such as sodium hydride. After about 1 to 2 hours, a solution of bromoamide of structure (13) or structure (14) in a suitable organic solvent, such as dimethylformamide is added to the mercaptide formed immediately above, as well as a suitable phase transfer catalyst, such as tetra-n-butylammonium iodide. The reaction mixture is stirred for 15 to 25 hours and saturated aqueous ammonium chloride solution and water are added. The cis α-thioamide of structure (15) or the trans α-thioamide of structure (16), respectively, may be isolated by methods well known and appreciated in the art, such as extraction and evaporation. The product can be purified by methods well known and appreciated in the art, such as flash chromatography.

In Scheme A, steps k1 and k2, cis α-thioamide of structure (15) and the trans α-thioamide of structure (16), respectively, are cleaved to provide the compounds of structures (17) and (18), respectively.

For example, a mixture of cis α-thioamide of structure (15) or the trans α-thioamide of structure (16), mercuric acetate and anisole in a suitable organic solvent, such as methylene chloride is cooled in an ice bath, degassed, and treated with a suitable acid, such as trifluoroacetic acid. After a time period of about 3–6 hours, hydrogen sulfide gas is bubbled in the reaction mixture for about 10 to 20 minutes. The compounds of structures (17) and (18) may be isolated by methods well known and appreciated in the art, such as extraction and evaporation. The product can be purified by methods well known and appreciated in the art, such as flash chromatography.

In Scheme A, optional steps l1 and l2, the thiol functionality of compounds (17) and (18) are acylated, if desired, with an R$_4$'-acylating agent wherein R$_4$' is defined as above, to provide the compounds (17a) and (18a).

For example, the appropriate compound of structures (17) or (18) can be contacted with a molar equivalent of an appropriate R$_4$'-acylating agent such as acetic anhydride and a catalytic amount of an acid such as sulfuric acid. The reactants are typically stirred together for a period of time ranging from 10 minutes to 10 hours. The compounds of structures (17a) and (18a) may be isolated by methods well known and appreciated in the art, such as extraction and evaporation. The products can be purified by methods well known and appreciated in the art, such as flash chromatography.

In Scheme A, step m, a compound of formula (17), (18), (17a), or (18a) is deprotected to give a compound of formula (1). Such deprotection reactions are well known appreciated in the art and may include selective deprotections in which the carboxy protecting group (Pg) and protecting groups on R$_1$, R$_2$, R$_3$, and R$_4$ are removed if desired.

R$_2$-substituted cyclohexanones of structure (2) can be prepared by utilizing techniques and procedures well known and appreciated by one of ordinary skill in the art. A general synthetic scheme for preparing these compounds is set forth in Scheme B wherein all substituents are as previously defined unless otherwise indicated.

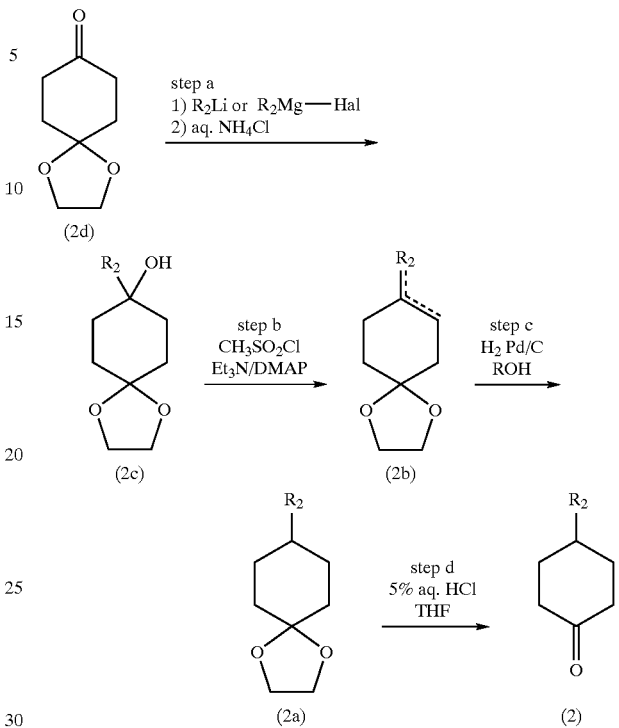

SCHEME B

Scheme B provides a general synthetic procedure for preparing compounds of formula (2) wherein the substituents are defined as above, unless otherwise indicated.

In Scheme B, step a, the ketone of structure (2d) is reacted with an organolithium compound of the formula R$_2$Li or a Grignard reagent of the formula R$_2$Mg-Hal, where "Hal" is halogen, according to techniques well known in the art to provide the tertiary alcohol of structure (2c).

For example, an appropriate Grignard reagent of structure R$_2$MgBr in a suitable organic solvent, such as ethyl ether is added to a solution of the ketone of structure (2d) in a suitable organic solvent, such as anhydrous ethyl ether. The reaction mixture is stirred and then cooled to about 0° C. Saturated ammonium chloride solution is then added. The ethereal layer is separated, washed with water and dried (MgSO$_4$). The solvent is evaporated in vacuo and purified by silica gel chromatography to give the tertiary alcohol of structure (2c).

An appropriate Grignard reagent of structure R$_2$Mg-Hal can be prepared by techniques well known in the art. For example, magnesium turnings and anhydrous ethyl ether are mixed under an inert atmosphere. A solution of a compound of the formula R$_2$-Hal, where "Hal" is halogen, in ethyl ether is then added to the magnesium mixture. The mixture is then stirred until the magnesium metal dissolves to give the Grignard reagent of structure R$_2$Mg-Hal.

In Scheme B, step b, the tertiary alcohol of structure (2c) is dehydrated according to techniques well known in the art to give the intermediate of structure (2b).

For example, the tertiary alcohol of structure (2c) may be dehydrated according to the procedure disclosed by Yadav, J. S. and Mysorekar, S. V., Synth. Comm. 19, 1057–1060 (1989). For example, to a stirred solution of the tertiary alcohol of structure (2c) in methylene chloride is added triethylamine and DMAP. The mixture is then cooled to about 0° C. and methanesulfonyl chloride is added dropwise to the mixture. The resulting reaction mixture is stirred for about 1 hour at room temperature. Crushed ice is added and the mixture stirred for about 1 hour. Afterwards, the reaction mixture is extracted with methylene chloride. The organic extracts are combined, washed with water and dried ($Na_2SO_4$). The solvent is then evaporated and the products are purified by methods well known and appreciated in the art, such as silica gel chromatography to provide the intermediate of structure (2b).

In Scheme B, step c, the intermediate of structure (2b) is reduced to provide the ketal of structure (2a).

For example, a solution of the intermediate of structure (2b) in a suitable organic solvent, such as methanol, may be treated with 10% palladium/carbon catalyst (Pd—C) and stirred under a hydrogen atmosphere for a period of from 10–20 hours. Additional catalyst may then be added, the mixture may be stirred for an additional 5–10 hours, degassed and filtered. The filtrate is then concentrated to yield the ketal of structure (2a).

In Scheme B, step d, the ketal of structure (2a) is hydrolyzed according to procedures well known in the art to provide the $R_2$-substituted cyclohexanone of structure (2). For example, the blocked ketone functionality of the compound of structure (2a) may be hydrolyzed according to the procedure disclosed by Honan, M. C., *Tetrahedron Lett.* 26, 6393–6396 (1985) or Greico, P. A. et al., *J. Amer. Chem. Soc.* 99, 5773–5780 (1977). For example, the ketal of structure (2a) is dissolved in a solution of a tetrahydrofuran/5% hydrochloric acid mixture (2:1) and allowed to react for a period of time ranging from about 15 to 25 hours at room temperature. The solvent is then removed under reduced pressure to afford the $R_2$-substituted cyclohexanone of structure (2).

The bromoacids of structure (12a) wherein $R_3$ is a W—$(CH_2)_m$— group are synthesized according to Scheme C. The bromoacid of structure (35) corresponds to the bromoacid of structure (12a) when $R_3$ is a W—$(CH_2)_m$— group. In Scheme 3, W is represented by PhtN, wherein W is phthalimido.

SCHEME C

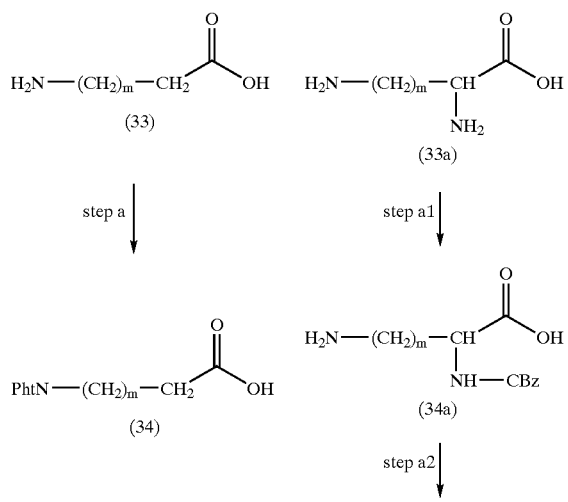

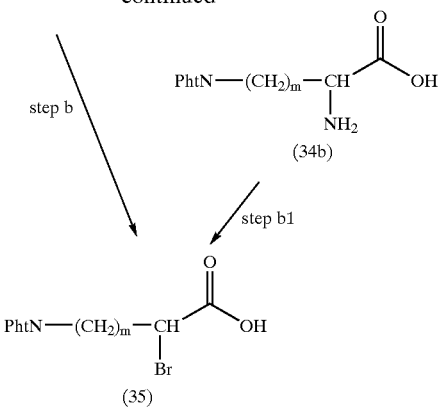

In Scheme C, step a, the amino carboxylic acid of structure (33) in a suitable polar solvent, such as water or a water/ethereal solvent mixture, is treated with sodium carbonate and N-carbethoxy phthalimide (NCEP). The reaction mixture is typically stirred at ambient temperature for 1–5 hours and extracted by extractive methods well known in the art. The aqueous layer is then cooled and acidified to about pH 1 using an acid, such as concentrated hydrochloric acid. The precipitate is then collected by filtration, washed with water and then dried to give the phthalimido carboxylic acid of structure (34).

In Scheme C, step b, the phthalimido carboxylic acid of structure (34) is brominated to give the 2-bromophthalimido carboxylic acid of structure (35). For example, a mixture of the phthalimido carboxylic acid of structure (34) and dry red phosphorous is treated dropwise with bromine at temperature ranging from about −20° to about 10° C. The reaction mixture is then warmed to room temperature and then heated to about 80° C. for about 2–5 hours. The reaction mixture is then cooled to room temperature, poured into water containing sodium bisulfite, and neutralized using solid $NaHCO_3$. The aqueous layer is washed with an ethereal solvent, such as diethyl ether, and acidified with a suitable acid, such as concentrated hydrochloric acid. The precipitate is collected by filtration and dried to yield the bromoacid of structure (35).

Alternatively, the bromoacid of structure (35) can be prepared following the procedure described in Scheme C, steps a1, a2 and b1, as described analogously by Baldwin, J. E. et al., *Tetrahedron* 44, 2633–2636 (1988) and Bezas, B. and Zervas, L., *J. Am. Chem. Soc.* 83, 719–722 (1961).

For example, in Scheme C, step a1, selective N-α-protection of a suitable α-amino acid, such as L-lysine, is accomplished by masking the ε-amino group by formation of a benzylidene imine. The benzylidene imine is formed by dissolving L-lysine monohydrochloride in lithium hydroxide and cooling the solution to a temperature ranging from about 0° to 10° C. Freshly distilled benzaldehyde is then added and the solution is shaken. N-ε-benzylidene-L-lysine is recovered by filtration and evaporation.

The α-amino group of the N-ε-benzylidene-L-lysine then undergoes urethane protection, followed by hydrolytic cleavage of the imine in situ to give N-α-benzyloxycarbonyl-L-lysine. For example, N-ε-benzylidene-L-lysine is added to a mixture of sodium hydroxide and ethanol, cooled to a temperature of from about −5° to about −25° C. Then, precooled solutions of benzyloxycarbonyl chloride in an alkaline solvent, such as sodium hydroxide and ethanol, are added to the reaction mixture. The temperature is maintained at a temperature ranging from about −10° to about −25° C. during the course of addition, and then allowed to rise slightly (approx. −5° C.) with stirring. The reaction mixture is then acidified using a suitable acid, such as precooled hydrochloric acid, and N-α-benzyloxycarbonyl-L-lysine, which corresponds to structure (34a) where m is 4, is recovered by filtration and recrystallization.

In Scheme C, step a2, N-α-benzyloxycarbonyl-L-lysine or other compounds of structure (34a) are reacted with N-carboethoxyphthalimide in aqueous sodium carbonate solution to yield optically pure phthaloyl derivatives of the compounds of structure (34a).

The phthaloyl derivatives of the compounds of structure (34a) are then reduced concurrently with carbobenzloxy hydrogenolysis to give the N-ε-phthaloyl amino acids of structure (34b). For example, the individual phthaloyl derivative of structure (34a) is contacted with a catalytic amount of a hydrogenation catalyst, such as 10% palladium/carbon. The reactants are typically contacted in a suitable solvent mixture such as tetrahydrofuran/water. The reactants are typically shaken under a hydrogen atmosphere of 35–45 psi at room temperature for a period of time ranging from 5–24 hours. The individual N-ε-phthaloyl amino acid of structure (34b) is recovered from the reaction zone by evaporation of the solvent.

In Scheme C, step b1, the individual N-ε-phthaloyl amino acid of structure (34b) is deaminobrominated to yield the bromoacid of structure (35). This reaction can be performed utilizing a reaction of the type described in Compagnone, R. S. and Rapoport, H., *J. Org. Chem.*, 51, 1713–1719 (1986); U.S. Pat. No. 5,322,942, issued Jun. 21, 1994; Overberger, C. G. and Cho, I., *J. Org. Chem.*, 33, 3321–3322 (1968); or Pfister, K. et al., *J. Am. Chem. Soc.*, 71, 1096–1100 (1949).

For example, a mixture of N-ε-phthaloyl amino acid of structure (34b) and a suitable bromide, such as hydrogen bromide or potassium bromide, in acidic solution, such as sulfuric acid, is treated with sodium nitrite. If avoidance of racemization caused by excess bromide ion is desired, the reaction temperature can be kept between −5° C. and 0° C. during addition and stirring. After the reaction mixture is stirred for a period of time ranging from 1.5 to 5 hours, the bromoacid of structure (35) may be recovered by extraction and evaporation.

The bromoacids of structure (12a) wherein $R_3$ is $C_1$–$C_6$ alkyl or a Q'—Z'—$(CH_2)_m$— group, wherein m is as defined above and Q' is hydrogen or a Y'—$(CH_2)_n$— group, wherein Y' is —$C(O)OR_6$; Z' is a bond, oxy or amino, are synthesized according to Scheme D. The bromoacid of structure (37) corresponds to the bromoacid of structure (12a) when $R_3$ is $C_1$–$C_6$ alkyl, or a Q'—Z'—$(CH_2)_m$— group.

The amino acids of structure (36), and N-protected forms thereof, are commercially available or may be readily prepared by techniques and procedures well known and appreciated by one of ordinary skill in the art. For example, L-alanine, D-alanine, L-valine, D-valine, D-norvaline, L-leucine, D-leucine, D-isoleucine, D-tert-leucine, glycine, L-glutamic acid, D-glutamic acid, L-glutamine, D-glutamine, L-lysine, D-lysine, L-ornithine, D-ornithine, (D)-(−)-2-aminobutyric acid, D-threonine, D-homoserine, D-allothreonine, D-serine, D-2-aminoadipic acid, D-aspartic acid, D-glutamic acid, D-lysine hydrate, 2,3-diaminopropionic acid monohydrobromide, D-ornithine hydrochloride, D,L-2,4-diaminobutyric acid dihydrochloride, L-meta-tyrosine, D-4-hydroxyphenylglycine, D-tyrosine, D-phenylalanine, D,L-2-fluorophenylalanine, beta-methyl-D,L-phenylalanine hydrochloride, D,L-3-fluorophenylalanine, 4-bromo-D,L-phenylalanine, D-2-phenylglycine, D,L-4-fluorophenylalanine, 4-iodo-D-phenylalanine, D-homophenylalanine, D,L-2-fluorophenylglycine, D,L-4-chlorophenylalanine, and the like, are all commercially available from Sigma Chemical Co., St. Louis, Mo. or Aldrich Chemical Co., Inc.

The cis α-thioamide of structure (15), the trans α-thioamide of structure (16), and the α-thioamide of structure (31) where $R_3$ is a $Q'^2$—$Z'^2$—$(CH_2)_m$— group wherein $Q'^2$ is a $Y'^2$—$(CH_2)_n$— group, where $Y'^2$ is —$N(R_6)_2$, can be synthesized according to techniques well known and appreciated by one of ordinary skill in the art. A general synthetic scheme for preparing these compounds is set forth in Scheme F wherein all substituents, unless otherwise indicated, are previously defined. The α-thioamide of structure (38) generically represents the cis α-thioamide of structure (15), the trans α-thioamide of structure (16), and the α-thioamide of structure (31) when $R_1$ is a $Q'^2$—$Z'^2$—$(CH_2)_m$— group wherein $Q'^2$ is a $Y'^2$—$(CH_2)_n$— group, where $Y'^2$ is —$N(R_6)_2$.

Schemes F–Q provide for compounds which give rise to compounds of formula (1) upon deprotection or selective deprotection of the carboxy protecting group, Pg. Such deprotections or selective deprotection reactions are well known appreciated in the art.

Scheme F provides compounds of structure (39) and (40) which give rise to compounds of formula (1) in which Z is an amine or a substituted amine. Scheme F also provides compounds of structure (41) which give rise to commands of formula (1) in which Z is a bond and Q is —$N(R_6)_2$.

SCHEME D

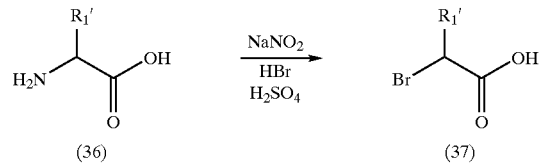

(36)　　　　　　　(37)

Scheme D provides a general synthetic procedure for preparing the bromoacids of structure (12a) when $R_3$ is $C_1$–$C_6$ alkyl or a Q'—Z'—$(CH_2)_m$— group, signified as structure (37). The substituent $R_3'$ is defined as $C_1$–$C_6$ alkyl, or a Q'—Z'—$(CH_2)_m$— group.

In Scheme D, an appropriate amino acid of structure (36) is deaminobrominated to yield the $R_3'$-substituted bromoacid of structure (37) as described previously in Scheme C, step b1.

SCHEME F

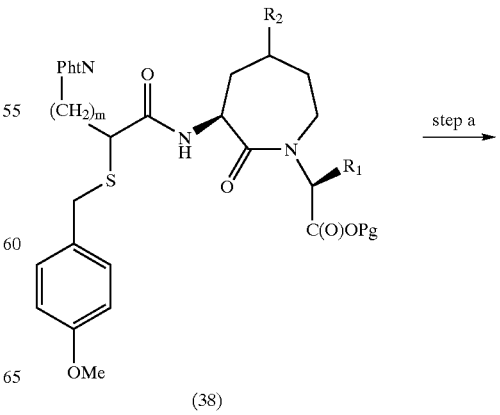

(38)

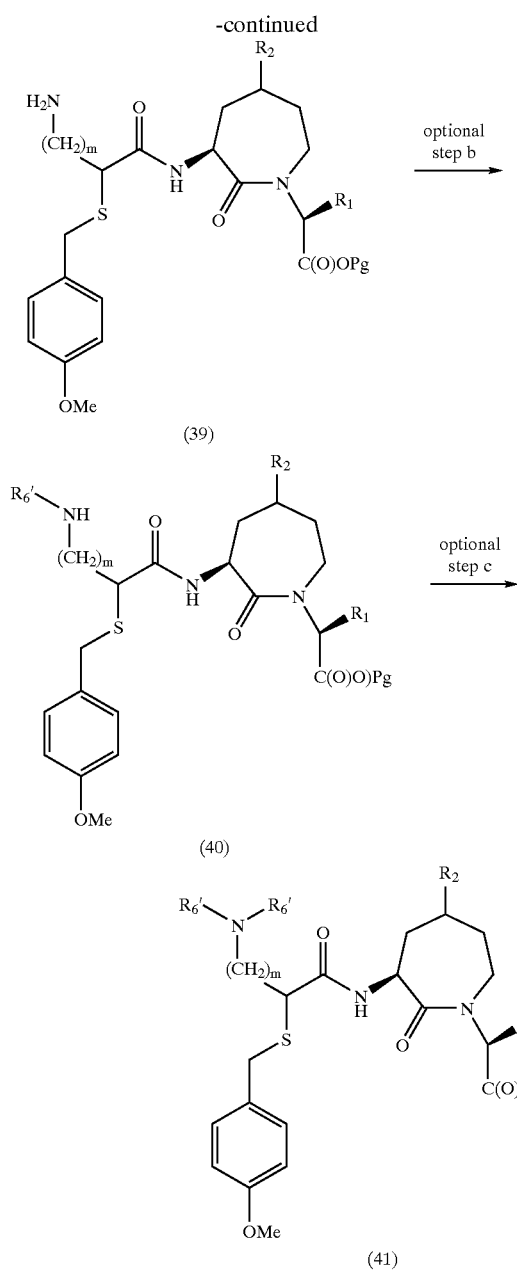

(39)

(40)

(41)

Scheme F provides a general synthetic procedure for preparing compounds of structures (15), (16) and (41) wherein $R_3$ is a $Q'^2$—$Z'^2$—$(CH_2)_m$— group wherein $Q'^2$ is a $Y'^2$—$(CH_2)_n$— group, where $Y'^2$ is —$N(R_6)_2$, and $Z'^2$ is a bond. All of the substituents are as defined above except $R_6'$ which is defined as $C_1$–$C_6$ alkyl.

In Scheme F, step a, the phthalimido group of the appropriate individual α-thioamide compounds of structure (38) is contacted with a molar excess of hydrazine monohydrate. The reactants are typically contacted in a protic organic solvent, such as methanol. The reactants are typically stirred together at room temperature for a period of time ranging from 5–24 hours. The corresponding free amine compounds of structure (39) are recovered from the reaction zone by evaporation of the solvent, redissolving in chloroform, filtration to remove phthal-hydrazide and removal of the chloroform in vacuo.

In Scheme F, optional step b, the individual free amines of structure (39) are converted to the $R_6'$-substituted amines of structure (40) by reductive alkylation.

For example, a mixture of the free amine of structure (39) in a protic organic solvent, such as methanol, is contacted with $R_6'$CHO, sodium cyanoborohydride and 1 drop of 1% bromocresol green in methanol. The pH of the reaction is maintained with 1N hydrochloric acid in methanol. The $R_6'$-substituted amines of structure (40) are recovered from the reaction zone by extraction and evaporation of the solvent.

In Scheme F, optional step c, the $R_6'$-substituted amines of structure (40) is converted to the di-$R_6'$-substituted amines of structure (41) as described above in Scheme D, optional step b.

The cis α-thioamide of structure (15), the trans α-thioamide of structure (16), and the α-thioamide of structure (41) where $R_3$ is a $Q'^3$—$Z'^3$—$(CH_2)_m$— group, wherein $Q'^3$ is a $Y'^3$—$(CH_2)_n$— group, $Z'^3$ is $CONR_6$, and $Y'^3$ is H, $C_6$–$C_{10}$ aryl, $C_3$–$C_9$ heteroaryl morpholino, piperidino, pyrrolidino or isoindolyl can be synthesized according to techniques well known and appreciated by one of ordinary skill in the art. A general synthetic scheme for preparing these compounds, signified as the compounds of structure (43), is set forth in Scheme G wherein all substituents, unless otherwise indicated, are previously defined.

SCHEME G

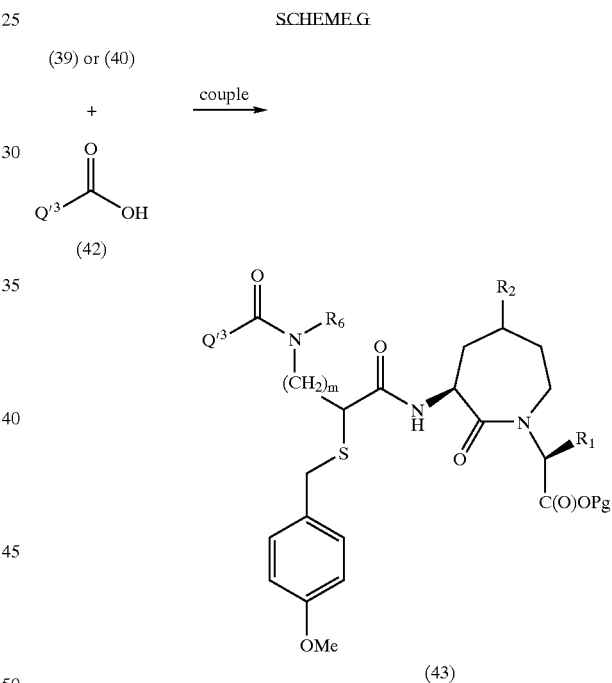

(43)

Scheme G provides a general synthetic procedure for preparing compounds of structures (15), (16) and (41) wherein $R_3$ is a $Q'^3$—$Z^3$—$(CH_2)_m$— group wherein $Q'^3$ is a $Y'^3$—$(CH_2)_n$— group, $Z'^3$ is $CONR_6$, and $Y'^3$ is H, $C_6$–$C_{10}$ aryl, $C_3$–$C_9$ heteroaryl, morpholino, piperidino, pyrrolidino or isoindolyl. All of the other substituents are as previously defined.

In Scheme G, the compounds of structure (43) are prepared by coupling the free amine of structure (39) or the $R_6'$-substituted amines of structure (40) with the acid of structure (42). Specifically, an acid of structure (42) is contacted with 1.2 to 1.7 equivalents of a suitable base, such as N-methylmorpholine, in a suitable solvent, such as tetrahydrofuran. The reaction mixture is cooled to a temperature of between −50° C. and 0° C. with −25° C. to −20° C. being preferred, before the addition of 1.2 to 1.7 equivalents of isobutyl chloroformate. The reaction is allowed to stir for 30 minutes to 3 hours to allow for the formation of the mixed anhydride, an activated intermediate. While maintaining the temperature at between −50° C. and 0° C., an appropriate free amine of structure (39) or an appropriate $R_6$'-substituted amines of structure (40) is added. The reaction may, after the addition of amine of structures (39) or (40) is complete, be warmed to room temperature. The reaction requires from 2 to 48 hours. The product (43) can be isolated and purified by techniques well known in the art, such as extraction, evaporation, chromatography, and recrystallization.

Alternatively, for example, an acid of structure (42) is contacted with thionyl chloride or oxalyl chloride to provide an acid chloride intermediate. The reaction is carried out using thionyl chloride or oxalyl chloride as a solvent or the reaction can be carried out in a suitable solvent, such as toluene, benzene, dichloromethane, carbon tetrachloride, or chloroform. The reaction may be carried out in the presence of a suitable catalyst, such as dimethylformamide or pyridine. The reaction is carried out at temperatures of from −40° C. to the refluxing temperature of the solvent. The reaction generally requires from 30 minutes to 24 hours. The acid chloride intermediate can isolated and purified by techniques well known in the art, such as evaporation, extraction, chromatography, and recrystallization.

The acid chloride intermediate is then contacted with an appropriate amine of structures (39) or (40). The reaction is carried out in a suitable solvent, such as toluene, tetrahydrofuran, dimethylformamide, dichloromethane, pyridine, or chloroform. The reaction is carried out in the presence of a slight molar excess of a suitable base, such as triethylamine, sodium carbonate, potassium bicarbonate, pyridine or diisopropylethyl amine. The reaction is carried out at a temperature of from −70° C. to the refluxing temperature of the solvent. The reaction generally requires from 30 minutes to 24 hours. The product of structure (43) can be isolated and purified by techniques well known in the art, such as extraction, evaporation, chromatography, and recrystallization.

Alternatively, for example, an acid of structure (42) is contacted with a slight molar excess of an appropriate amine of structures (39) or (40) and 1-hydroxybenzotriazole hydrate in the presence of a slight molar excess of a coupling agent, such as dicyclohexylcarbodiimide (DCC) or 1-(3-dimethylaminopropyl)-3-ethylcarbodiimide (EDC). The reaction is carried out in the presence of a suitable base, such as diisopropylethyl amine. The reaction is carried out in a suitable solvent, such as dichloromethane or chloroform. The product can be isolated and purified by techniques well known in the art, such as extraction, evaporation, chromatography, and recrystallization.

The compounds of structure (42), and activated intermediates thereof, are commercially available or may be readily prepared by techniques and procedures well known and appreciated by one of ordinary skill in the art. For example, benzoic acid, 1-naphthoic acid, 2-naphthoic acid, quinaldic acid, 4-pyridazine-carboxylic acid, 4-pyrazolecarboxylic acid, 2-furoic acid, 3-furoic acid, 2-pyrazinecarboxylic acid, 2-thiophenecarboxylic acid, 4-morpholinecarbonyl chloride, Boc-isonipecotic acid, isonicotinic acid, and picolinic acid are commercially available from Aldrich Chemical Co., Inc and Baychem, Inc.

The cis α-thioamide of structure (15), the trans α-thioamide of structure (16), and the α-thioamide of structure (41) where $R_3$ is a $Q'^3—Z'^4—(CH_2)_m—$ group, wherein $Q'^3$ is as defined in Scheme G, m is defined previously and $Z'^4$ is $NHC(O)NR_6$, can be synthesized according to techniques well known and appreciated by one of ordinary skill in the art. A general synthetic scheme for preparing these compounds, signified as the compounds of structure (45), is set forth in Scheme H wherein all substituents, unless otherwise indicated, are previously defined.

SCHEME H

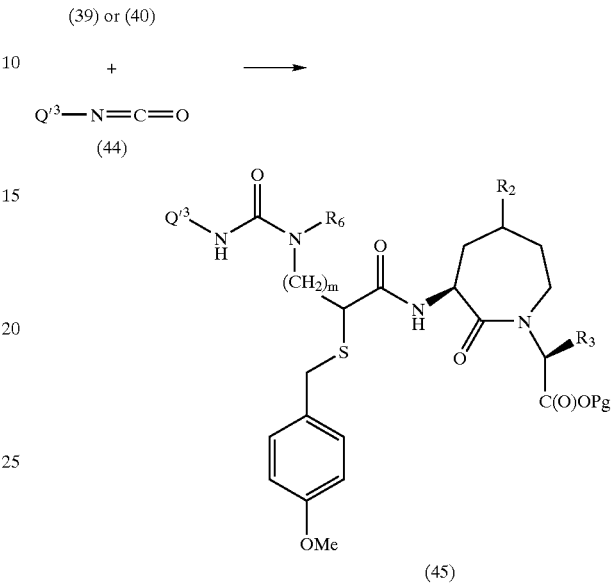

(45)

Scheme H provides a general synthetic procedure for preparing compounds of structures (15), (16) and (41) wherein $R_3$ is a $Q'^3—Z'^4—(CH_2)_m—$ group, wherein $Q'^3$ is as defined in Scheme G, m is defined previously and $Z'^4$ is $NHC(O)NR_6$. All of the other substituents are as defined above.

In Scheme H, the compounds of structure (45) are prepared by reacting a free amine of structure (39) or a $R_6$'-substituted amine of structure (40) with the isocyanate of structure (44). For example, an equivalent of, or a slight molar excess of, an appropriate isocyanate of structure (44) is added to a solution of an appropriate free amine of structure (39) or an appropriate $R_6$'-substituted amine of structure (40) in a suitable dry aromatic solvent, such as anhydrous benzene or anhydrous toluene. The mixture is then refluxed for a period of time ranging from 2–24 hours. The appropriate compound of structure (45) can be isolated and purified by techniques well known in the art, such as extraction, evaporation, chromatography, and recrystallization.

The compounds of structure (44), and activated intermediates thereof, are commercially available or may be readily prepared by techniques and procedures well known and appreciated by one of ordinary skill in the art. For example, phenyl isocyanate and 1-naphthyl isocyanate are available from Aldrich Chemical Co., Inc. Other compounds of structure (44) which are known in the art include 4-methyphenyl isocyanate, 4-methoxyphenyl isocyanate, 2-naphthyl isocyanate, 4-aminophenyl isocyanate, 4-fluorophenyl isocyanate, 3-chlorophenyl isocyanate, 4-chlorophenyl isocyanate, 3,4-dichlorophenyl isocyanate, 2,6-dimethylphenyl isocyanate, 2-methoxy-1-naphthyl isocyanate, 2,4,6-trimethylphenyl isocyanate and 4-nitrophenyl isocyanate.

The cis α-thioamide of structure (15), the trans α-thioamide of structure (16), and the α-thioamide of structure (41) where $R_3$ is a $Q^3—Z'^5—(CH_2)_m—$ group, wherein $Q'^3$ is as defined in Scheme G, m is defined previously and $Z'^5$ is $OC(O)NR_6$, can be synthesized according to techniques well known and appreciated by one of ordinary skill in the art. A general synthetic scheme for preparing these compounds, signified as the compounds of structure (48), is set forth in Scheme I wherein all substituents, unless otherwise indicated, are previously defined.

SCHEME I

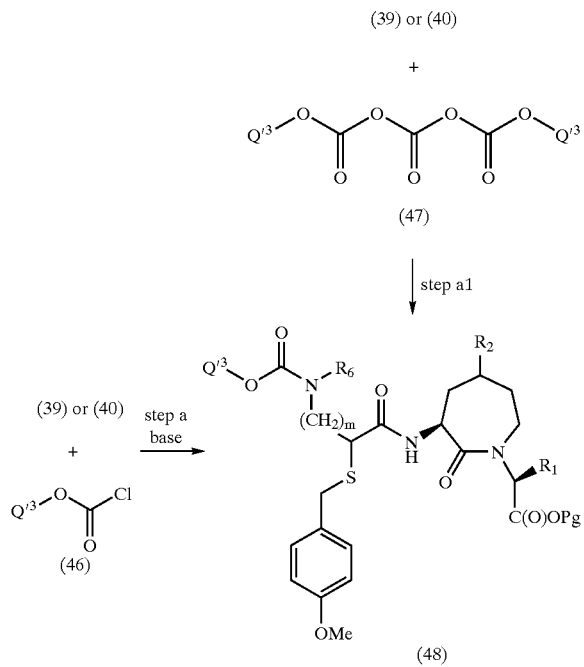

(48)

Scheme I provides a general synthetic procedure for preparing compounds of structures (15), (16) and (41) wherein $R_3$ is a $Q'^3$—$Z'^5$—$(CH_2)_m$— group, wherein $Q'^3$ is as defined in Scheme G, m is defined previously and $Z'^5$ is $OC(O)NR_6$. All of the other substituents are as defined above.

In Scheme I, step a, an appropriate free amine of structure (39) or an appropriate $R_6'$-substituted amine of structure (40) is coupled to the chloroformate of structure (46) in the presence of a suitable solvent, such as toluene, tetrahydrofuran, dimethylformamide, dichloromethane, pyridine, or chloroform. The reaction is carried out in the presence of a slight molar excess of a suitable base, such as triethylamine, sodium carbonate, potassium bicarbonate, pyridine or diisopropylethylamine. The reaction is carried out at a temperature of from −70° C. to the refluxing temperature of the solvent. The reaction generally requires from 30 minutes to 24 hours. The product of structure (48) can be isolated and purified by techniques well known in the art, such as extraction, evaporation, chromatography, and recrystallization.

The chloroformates of structure (46) are commercially available or may be readily prepared by techniques and procedures well known and appreciated by one of ordinary skill in the art. For example, phenyl chloroformate, benzyl chloroformate, 4-chlorophenyl chloroformate, 4-nitrophenyl chloroformate, 4-methylphenyl chloroformate, 4-bromophenyl chloroformate, 4-fluorophenyl chloroformate, 4-methoxyphenyl chloroformate and chloroformic acid 2-naphthyl ester are available from Aldrich Chemical Co., Inc., or are otherwise known in the art.

Alternatively, in Scheme I, step a1, an appropriate free amine of structure (39) or an appropriate $R_6'$-substituted amine of structure (40) is reacted with the anhydride of structure (47) according to the anhydride coupling procedure described previously in Scheme G.

The anhydrides of structure (47) may be readily prepared by techniques and procedures well known and appreciated by one of ordinary skill in the art. See for example, Pope, B. M. et al., *Org. Synth.*, VI, 418 (1988); Dean, C. S. et al., *Chem. Comm.*, 728 (1969); Tarbell, D. S. et al., *Proc. Natl. Acad. Sci.* (*USA*) 69, 730 (1972) or Dean, C. S. et al., *J. Org. Chem.* 35, 3393 (1970).

The cis α-thioamide of structure (15), the trans α-thioamide of structure (16), and the α-thioamide of structure (41) where $R_3$ is a $Q'^3$—$Z'^6$—$(CH_2)_m$— group, wherein $Q'^3$ is as defined in Scheme G, m is defined previously and $Z'^6$ is $SO_2NR_6$, can be synthesized according to techniques well known and appreciated by one of ordinary skill in the art. A general synthetic scheme for preparing these compounds, signified as the compounds of structure (51), is set forth in Scheme J wherein all substituents, unless otherwise indicated, are previously defined.

SCHEME J

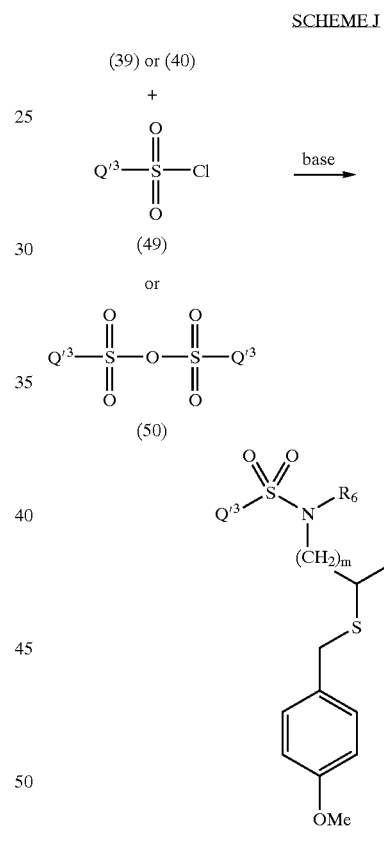

(51)

Scheme J provides a general synthetic procedure for preparing compounds of structures (15), (16) and (41) wherein $R_3$ is a $Q'^3$—$Z'^6$—$(CH_2)_m$— group, wherein $Q'^3$ is as defined in Scheme G, m is defined previously and $Z'^6$ is $SO_2NR_6$. All of the other substituents are as defined above.

In Scheme J, an appropriate free amine of structure (39) or an appropriate $R_6'$-substituted amine of structure (40) is reacted with the with the chloride of structure (49) or the anhydride of structure (50) according to the anhydride coupling procedure described previously in Scheme G.

The chlorides of structure (49) are commercially available or may be readily prepared by techniques and procedures well known and appreciated by one of ordinary skill in the art. For example, benzenesulfonyl chloride, 1-napthalenesulfonyl chloride, 2-napthalenesulfonyl chloride, dansyl chloride, 8-quinolinesulfonyl chloride, 2-dibenzofuransulfonyl chloride, 1,2-napthoquinone-2-diazide-4-sulfonyl chloride, N-morpholinylsulfonyl chloride, N-piperidinylsulfonyl chloride, 2,4,5-trichlorobenzenesulfonyl chloride, 2,5-dichlorobenzenesulfonyl chloride, 2-nitrobenzenesulfonyl chloride, 2,4-dinitrobenzenesulfonyl chloride, 3,5-dichloro-2-hydroxybenzenesulfonyl chloride, 2,4,6-triisopropylbenzenesulfonyl chloride, 2-mesitylenesulfonyl chloride, 3-nitrobenzenesulfonyl chloride, 4-bromobenzenesulfonyl chloride, 4-fluorobenzenesulfonyl chloride, 4-chlorobenzenesulfonyl chloride, 4-chloro-3-nitrobenzenesulfonyl chloride, 4-nitrobenzenesulfonyl chloride, 4-methoxybenzenesulfonyl chloride, 4-t-butylbenzenesulfonyl chloride, p-toluenesulfonyl chloride, 2,3,4-trichlorobenzenesulfonyl chloride, 2,5-dimethoxybenzenesulfonyl chloride, 4-ethylbenzenesulfonyl chloride, 3,4-dimethoxybenzenesulfonyl chloride, 2,6-dichlorobenzenesulfonyl chloride, 3-bromobenzenesulfonyl chloride, 4-methoxy-2-nitrobenzenesulfonyl chloride and 4-n-butylbenzenesulfonyl chloride are available from Aldrich Chemical Co., Inc., other chemical suppliers, such as Lancaster, Salor, or Maybridge, or are otherwise known in the art.

The anhydrides of structure (50) are commercially available or may be readily prepared by techniques and procedures well known and appreciated by one of ordinary skill in the art. For example, benzenesulfonic anhydride, 4-toluenesulfonic anhydride, 2-mesitylenesulfonic anhydride and 4-nitrobenzenesulfonic anhydride are available from Aldrich Chemical Co., Inc., or are otherwise known in the art.

The cis α-thioamide of structure (15), the trans α-thioamide of structure (16), and the α-thioamide of structure (41) where $R_3$ is a $Q'^3$—$Z'^7$—$(CH_2)_m$— group, wherein $Q'^3$ is as defined in Scheme G, m is defined previously and $Z'^7$ is $NR_6C(O)$, can be synthesized according to techniques well known and appreciated by one of ordinary skill in the art. A general synthetic scheme for preparing these compounds, signified as the compounds of structure (54), is set forth in Scheme K wherein all substituents, unless otherwise indicated, are previously defined.

SCHEME K

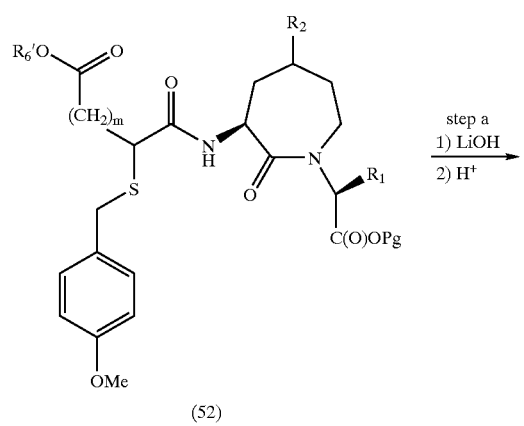

(52)

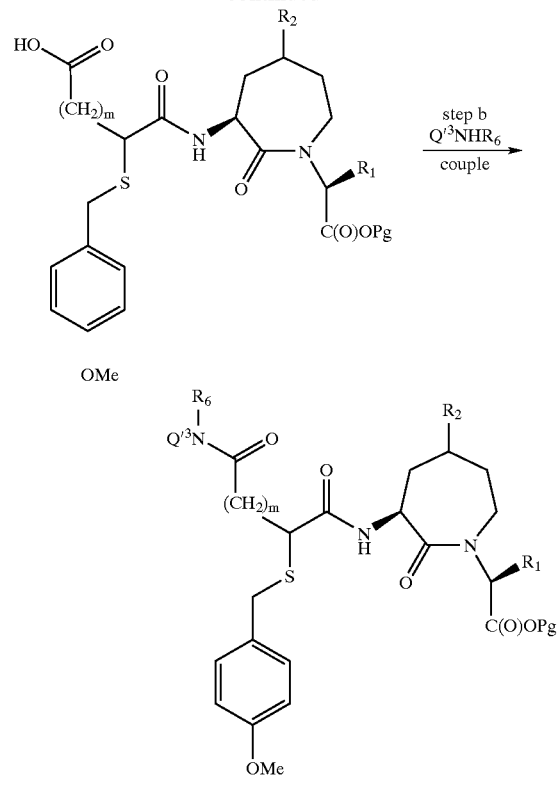

(54)

Scheme K provides a general synthetic procedure for preparing compounds of structures (15), (16) and (41) wherein $R_3$ is a $Q'^3$—$Z'^7$—$(CH_2)_m$— group, wherein $Q'^3$ is as defined in Scheme G, m is defined previously and $Z'^7$ is $NR_6C(O)$. All of the other substituents are as defined above.

In Scheme K, step a, an appropriate ester of structure (52) is deprotected under conditions well known in the art to provide the acid of structure (53). For example, when $R_6'$ is methyl or ethyl, the ester of structure (52) is dissolved in a suitable organic solvent, such as ethanol and treated with approximately an equal volume of water. To this solution, with stirring is added 1 to 2 equivalents of lithium hydroxide and the reaction is allowed to stir for 1 to 6 hours. The resulting acid is then isolated and purified by techniques well known in the art. For example, the organic solvent is removed under vacuum and the remaining aqueous solution is acidified with dilute hydrochloric acid. The aqueous phase is then extracted with a suitable organic solvent, such as ethyl acetate, and the combined organic extracts are dried over anhydrous magnesium sulfate, filtered and concentrated under vacuum. The residue can then be purified by flash chromatography on silica gel with a suitable eluent, such as methanol/chloroform to provide the acid of structure (53).

In Scheme K, step b, the acid of structure (53) is coupled with the amine of structure (53a) under conditions well known in the art to provide the retroamide of structure (54). For example, the acid of structure (53) is dissolved in a suitable organic solvent, such as methylene chloride, under an inert atmosphere, such as nitrogen. The solution is then treated with one to four equivalents of a suitable amine, such as N-methylmorpholine, cooled to about −20° C. and one equivalent of isobutylchloroformate is added. The reaction is allowed to stir for about 10 to 30 minutes and 1 to 4 equivalents of the amine of structure (53a) is added to the reaction. The reaction is stirred for 30 minutes to 2 hours at about −20° C. and then it is allowed to warm to room temperature and stir for 1 to 3 hours. The retroamide (54) is then isolated and purified by techniques well known in the art, such as extractive techniques and flash chromatography. For example, the reaction is diluted with a suitable organic solvent such as methylene chloride, rinsed with water, dried over anhydrous magnesium sulfate, filtered and concentrated under vacuum. The residue is purified by flash chromatography on silica gel with a suitable eluent, such as ethyl acetate/hexane to provide the retroamide (54).

Alternatively, the amine of structure (53a) is dissolved in a suitable anhydrous organic solvent, such as methylene chloride under an inert atmosphere, such as nitrogen. To this solution is added an equivalent of N-hydroxybenztriazole hydrate, an equivalent of 1-(3-dimethylaminopropyl)-3-ethylcarbodiimide hydrochloride and an equivalent of the acid of structure (53), dissolved in a suitable anhydrous organic solvent, such as methylene chloride. The reaction is then allowed to stir for about 1 to 15 hours. The retroamide of structure (54) is then isolated and purified by techniques well known in the art, such as extractive techniques and flash chromatography. For example, the reaction is diluted with a suitable organic solvent, such as ethyl acetate, rinsed with water, dried over anhydrous magnesium sulfate, filtered and concentrated under vacuum. The residue is purified by flash chromatography on silica gel with a suitable eluent, such as ethyl acetate/hexane to provide the retroamide (54).

The cis α-thioamide of structure (15), the trans α-thioamide of structure (16), and the α-thioamide of structure (41) where $R_3$ is a $Q'^3$—$Z'^8$—$(CH_2)_m$— group, wherein $Q'^3$ is as defined in Scheme G, m is defined previously and $Z'^8$ is HNC(O)O, can be synthesized according to techniques well known and appreciated by one of ordinary skill in the art. A general synthetic scheme for preparing these compounds, signified as the compounds of structure (56), is set forth in Scheme L wherein all substituents, unless otherwise indicated, are previously defined.

SCHEME L

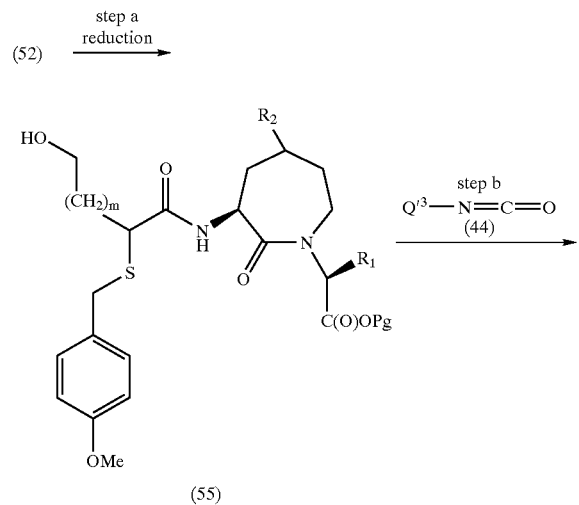

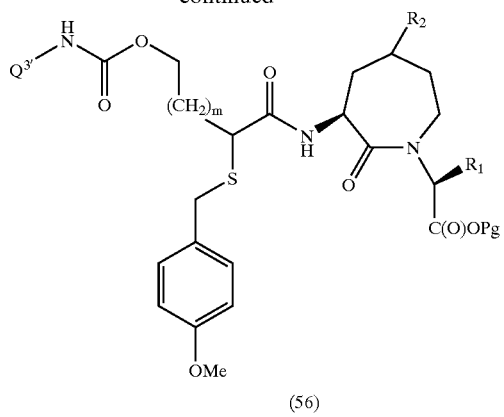

Scheme L provides a general synthetic procedure for preparing compounds of structures (15), (16) and (41) wherein $R_3$ is a $Q'^3$—$Z'^8$—$(CH_2)_m$— group, wherein $Q'^3$ is as defined in Scheme G, m is defined previously and $Z'^8$ is HNC(O)O. All of the other substituents are as defined above.

In Scheme L, step a, an appropriate ester of structure (52) is reduced under conditions well known in the art to provide the alcohol of structure (55). For example, the ester of structure (52) is dissolved in a suitable solvent, such as hexane, dichloromethane, tetrahydrofuran or toluene, with tetrahydrofuran being preferred, and contacted with a suitable reducing agent, such as lithium borohydride, sodium borohydride, lithium aluminum hydride, diisobutylaluminum hydride, 9-borabicyclo[3.3.1]nonane, preferably lithium borohydride. The reaction is carried out by either adding a solution of an appropriate ester (52) to a solution of an appropriate reducing agent or by adding a solution of an appropriate reducing agent to a solution of an appropriate ester of structure (52). The addition is carried out at a temperature of from about −30° C. to about 10° C. The reaction is carried out at a temperature of from about 0° C. to about 30° C. The reaction generally requires from 2 to 5 hours. The product can be isolated by quenching and extraction. The quench is carried out at a temperature of from about −15° C. to about 0° C. The alcohol of structure (55) can be isolated by methods well known and appreciated in the art, such as extraction and evaporation. The alcohol of structure (55) can be purified as is well known in the art by chromatography and distillation.

In Scheme L, step b, the alcohol of structure (55) is reacted with the isocyanate of structure (44) according to the procedures set forth in Scheme H above to afford the appropriate compound of structure (56).

Alternatively, the cis α-thioamide of structure (15), the trans α-thioamide of structure (16), and the α-thioamide of structure (41) can be synthesized according to techniques well known and appreciated by one of ordinary skill in the art. An alternate general synthetic scheme for preparing these compounds is set forth in Scheme M wherein all substituents, unless otherwise indicated, are previously defined.

SCHEME M

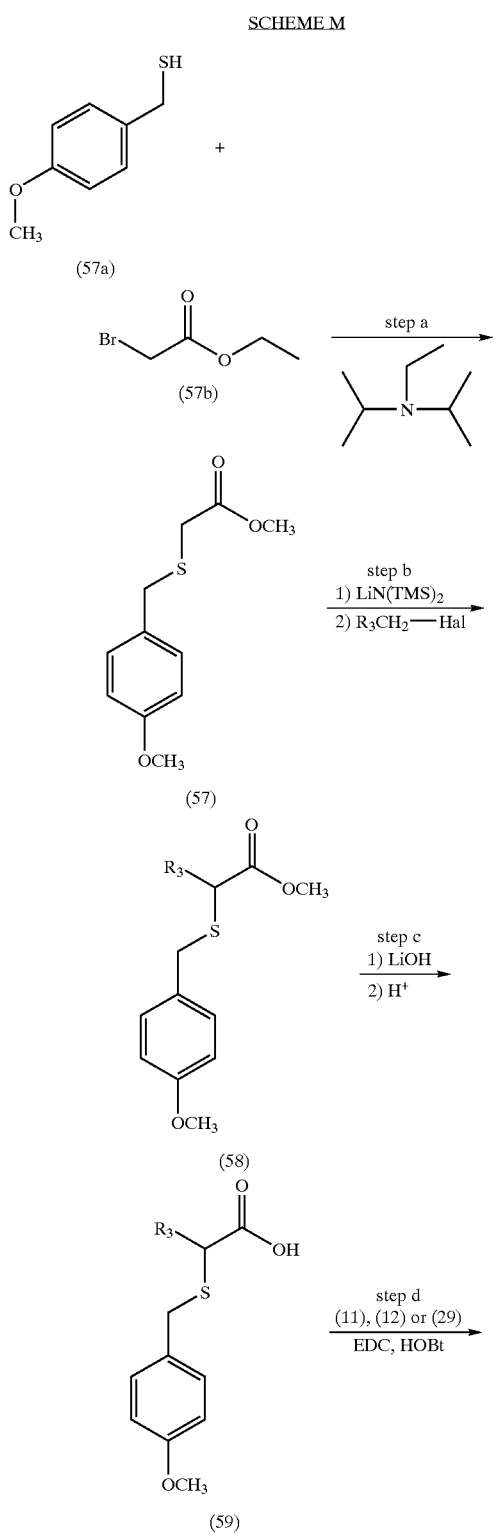

Scheme M provides an alternate general synthetic procedure for preparing compounds of structures (15), (16) and (41). All of the substituents are as defined above.

In Scheme M, step a, the thiol of structure (57a) in a suitable organic solvent such as dimethylformamide, is degassed and treated with ethyl bromoacetate (57b) and a suitable tertiary amine such as diisopropylethylamine. The reaction mixture is placed in a cooling bath and stirred for a period of time ranging from about 20 minutes to about 1 hour whereupon a precipitate is observed. The cooling bath is then removed and the reaction mixture is stirred for an additional 48 to 72 hours. The sulfide ester of structure (57) can be isolated by methods well known and appreciated in the art, such as extraction and evaporation. The sulfide ester of structure (57) can be purified as is well known in the art by chromatography and distillation.

In Scheme M, step b, the sulfide ester of structure (57) in a suitable organic solvent such as tetrahydrofuran is treated with an amide base such as lithium bis(trimethylsilyl)amide. The resulting intermediate is then reacted with an $R_3$-substituted alkyl halide ($R_3CH_2$-Hal) to yield the $R_3$-substituted sulfide ester of structure (58). The $R_1$-substituted sulfide ester of structure (58) can be isolated by methods well known and appreciated in the art, such as extraction and evaporation. The $R_3$-substituted sulfide ester of structure (58) can be purified as is well known in the art by chromatography and distillation.

In Scheme M, step c, the $R_3$-substituted sulfide ester of structure (58) is deprotected to yield the $R_1$-substituted sulfide acid of structure (59) according to the procedure described in Scheme K, step a.

In Scheme M, step d, the $R_3$-substituted sulfide acid of structure (59) is coupled with an appropriate compound of structures (11), (12) or (29) to provide an appropriate compound of structures (15), (16) or (41) according the procedures described in Scheme G.

The compounds of formula (1) wherein $R_4$ is a —C(O)—$(CH_2)_q$—K group can be synthesized according to techniques well known and appreciated by one of ordinary skill in the art, as disclosed in U.S. Pat. No. 5,424,425, issued Jun. 13, 1995. A general synthetic scheme for preparing these compounds, signified as the compounds of structure (61), is set forth in Scheme N wherein all substituents, unless otherwise indicated, are previously defined.

SCHEME N

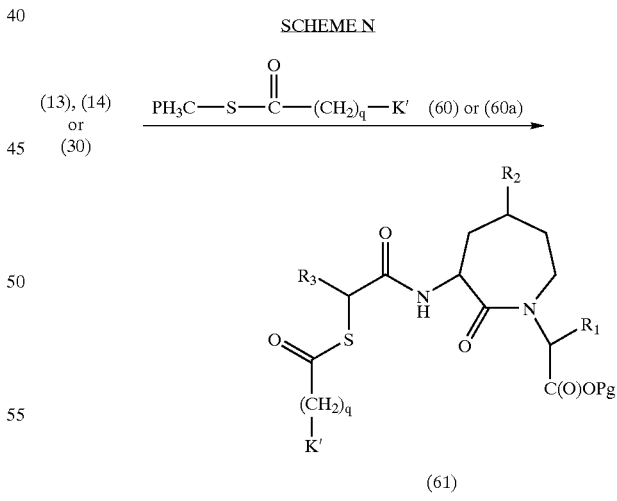

Scheme N provides a general synthetic procedure for preparing compounds of structure (61) wherein K' is

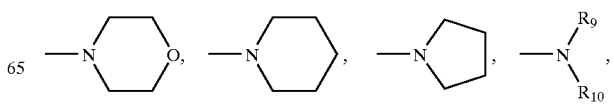

R$_7$" represents Boc, C$_1$–C$_4$ alkyl or a —(CH$_2$)$_p$—Ar$_2$ group. All of the other substituents are as defined above.

In Scheme N the appropriate thioacetyl compound of structure (61) can be prepared by reacting the appropriate bromoamide of structure (13), (14) or (30) with the appropriate triphenylmethyl aminothiolacetate of structure (60 or 60a) under basic conditions such as sodium hydride, hydrogen sulfide in a suitable aprotic solvent such as dimethylformamide.

For those thioacetyl compounds of structure (61) wherein K' is

wherein R$_7$' is Boc, the Boc protecting group can be removed using trifluoroacetic acid to give the corresponding compounds where R$_7$ is hydrogen.

In addition, the sulfide functionality of those thioacetyl compounds of structure (61) wherein K' is

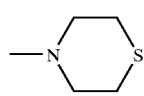

may be oxidized by techniques and procedures well known in the art, such as magnesium monoperoxyphthalic acid hexahydrate to give the thioacetyl compounds of structure (61) wherein K is

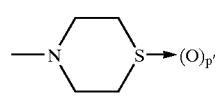

wherein p' is 1 or 2.

Scheme O provides a general synthetic scheme for preparing the triphenylmethyl aminothiolacetates of structures (60) and (60a).

SCHEME O

Scheme O provides a general synthetic procedure for preparing compounds of structure (64) and (64a) wherein K" is

R$_7$" represents Boc, C$_1$–C$_4$ alkyl or a —(CH$_2$)$_p$—Ar$_2$ group. All of the other substituents are as defined above.

In Scheme O, step a, a triphenylmercaptan (62) and bromoacetyl bromide (63) are reacted under basic conditions, such as pyridine, in an aprotic solvent, such as methylene chloride to give triphenylmethylbromothiolacetate of structure (64).

In Scheme O, step b, triphenylmethyl bromothiolacetate of structure (64) is reacted with the appropriate amino compound of structure (65) under basic conditions, such as pyridine, in an aprotic solvent such as methylene chloride to give the appropriate triphenylmethyl aminothiolacetate compound of structure (66).

In Scheme O, optional step c, the sulfide functionality of those thioacetyl compounds of structure (66) wherein K" is

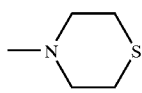

may be oxidized by techniques and procedures well known in the art, such as magnesium monoperoxyphthalic acid hexahydrate to give the thioacetyl compounds of structure (66a) wherein K is

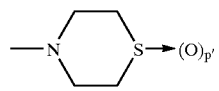

wherein p' is 1 or 2.

Alternatively, the compounds of formula (1) wherein $R_4$ is a —C(O)—(CH$_2$)$_q$—K group may be prepared as described in Scheme P. In Scheme P, all substituents are as previously defined unless otherwise indicated.

SCHEME P

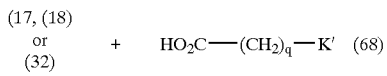

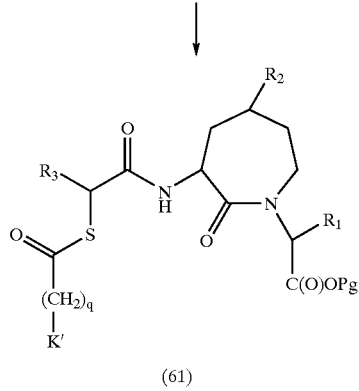

Scheme P provides a general synthetic procedure for preparing compounds of structure (61) wherein all of the substituents are as previously defined.

In Scheme P, the thiol functionality of the thiol compounds of structures (17), (18) or (32) is coupled with the appropriate acid of structure (68) in the presence of a suitable coupling agent to give the appropriate thioacetyl compound of structure (61). For example, the appropriate thiol compound of structures structures (17), (18) or (32) can be reacted with the appropriate acid of structure (68) in the presence of a coupling agent such as 2-fluoro-1-methylpyridinium p-toluenesulfate, EDC (1-(3-dimethylaminopropyl)-3-ethylcarbodiimide hydrochloride), carbonyldiimidazole, EEDQ (1-ethoxycarbonyl-2-ethoxy-1, 2-dihydroquinoline, DCC, or diethylcyanophosphonate in a suitable aprotic solvent such as methylene chloride to give the appropriate thioacetyl compound of structure (61).

The compounds of formula (1) wherein $R_4$ is a —S—G group can be synthesized according to techniques well known and appreciated by one of ordinary skill in the art, as disclosed in PCT Int. Publ. No. WO 95/21839, published Aug. 17, 1995. A general synthetic scheme for preparing these compounds, signified as the compounds of structure (71), is set forth in Scheme Q wherein all substituents, unless otherwise indicated, are previously defined.

SCHEME Q

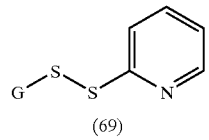

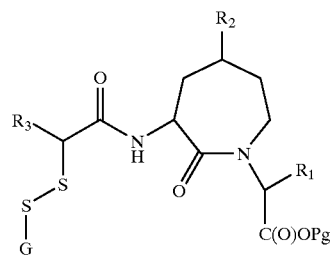

The disulfides of structure (69) can be obtained by methods Inown in the art or by methods known analogously in the art, Roques, B. P. et al., *J. Med. Chem.* 33, 2473–2481 (1992).

In Scheme Q, an appropriate disulfide of structure (69) is contacted with an appropriate thiol of structures (17), (18) or (32) to give a disulfide of structure (70) or a protected form thereof. An appropriate disulfide of structure (70) is one in which G is as desired in the final product of formula (1) or gives rise upon deprotection to G as is desired in the final product of formula (1).

For example, an appropriate disulfide of structure (69) is contacted with an appropriate thiol of structures (17), (18) or (32). The reaction is carried out in a suitable solvent, such as ethanol, methanol, dichloromethane, or mixtures of ethanol or methanol and dichloromethane. The solvent is degassed by passing a stream of nitrogen gas through it for 15 minutes before the reaction is carried out. The reaction is carried out using from 1.0 to 4.0 molar equivalents of an appropriate compound of structure (69). The reaction is carried out at temperatures of from 0° C. to the refluxing temperature of the solvent, with a temperature of 10° C. to 30° C. being preferred. The reaction generally requires from 1 to 48 hours. The product can be isolated by techniques well known in the art, such as extraction, evaporation, and precipitation. The appropriate disulfide or protected disulfide of structure (70) can be purified by chromatography and recrystallization.

The protected disulfides of structure (70) can be deprotected according to techniques well known in the art. The selection, use and removal of protecting groups and the removal of protecting groups in a sequential manner utilizing suitable protecting groups such as those described in *Protecting Groups in Organic Synthesis* by T. Greene is well known and appreciated by those skilled in the art.

The following preparations and examples present typical syntheses as described in Schemes A through Q. These examples are understood to be illustrative only and are not intended to limit the scope of the present invention in any way. As used herein, the following terms have the indicated meanings: "g" refers to grams; "mol" refers to moles; "mmol" refers to millimoles; "L" refers to liters; "mL" refers to milliliters; "bp" refers to boiling point; "° C." refers to degrees Celsius; "mm Hg" refers to millimeters of mercury; "mp" refers to melting point; "mg" refers to milligrams; "µM" refers to micromolar; "µg" refers to micrograms; "h" or "hrs." refers to hours, "min" refers to minutes; "HOBt" refers to hydroxybenzotriazole; "EDC" refers to 1-(3-dimethylaminopropyl)-3-ethylcarbodiimide hydrochloride; "NCEP" refers to N-carbethoxy phthalimide; and "MTBE" refers to methyl:tert-butyl ether.

PREPARATION 1

Synthesis of 2-bromo-6-phthalimidohexanoic acid

Combine 6-aminohexanoic acid (6-aminocaproic acid) (8.0 g, 60 mmol) and water (100 mL). Add sodium carbonate (6.84 g, 64 mmol) and N-carbethoxyphthalimide (14.0 g, 64 mmol). After 1.5 hours, extract the reaction mixture with ethyl acetate (100 mL). Cool the aqueous layer in an ice bath and acidify using concentrated hydrochloric acid to give a solid. Collect the solid by filtration, rinse with water, and dry to give 6-phthalimidohexanoic acid (12.7 g, 80% yield).

Combine 6-phthalimidohexanoic acid (12.7 g, 48 mmol) and dry red phosphorous (1.95 g, 63 mmol). Cool in an ice bath and add dropwise bromine (12.7 mL, 246 mmol). Warm to room temperature and then heat to 80° C. After 3 hours, cool the reaction mixture to ambient temperature, pour into water (300 mL) containing sodium bisulfite, and neutralize using solid sodium bicarbonate and extract with diethyl ether (about 150 mL). Acidify the aqueous layer with concentrated hydrochloric acid give a solid. Collect the solid by filtration and dry to give the title compound (15 g, 91.5% yield, 73.2% for both steps).

EXAMPLE 1

N-[Hexahydro-1-[1-(phenylmethyl)-1-carboxymethyl]-2-oxo-5-phenyl-1H-azepin-3-yl]-1,3-dihydro-α-mercapto-1,3-dioxo-2H-isoindole-2-hexanamide

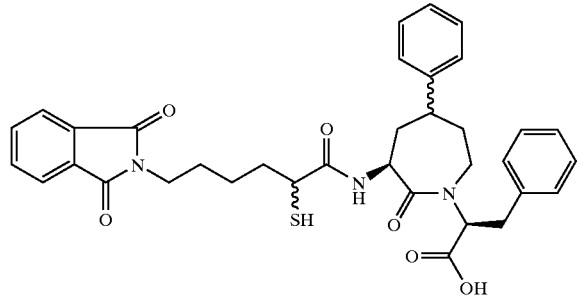

1.1 Synthesis of 1-trimethylsilyloxy-4-phenylcyclohex-1-ene

Combine diisopropylamine (16.2 mL, 116 mmol) and tetrahydrofuran (100 mL). Cool in an ice-bath. Add dropwise a solution of n-butyl lithium (44 mL, 2.5 M in hexane, 110 mmol). Cool in a dry-ice/acetone bath. Add a solution of 4-phenylcyclohexane-1-one (17.42 g, 100 mmol) in tetrahydrofuran (40 mL). After 1 hour, add trimethylsilyl chloride (14 mL, 110 mmol). After 45 minutes, warm to ambient temperature. After 2 hours, pour the reaction mixture onto ice water (about 100 mL)/saturated aqueous sodium bicarbonate (about 100 mL) and extract with pentane (300 mL). Extract the organic layer with brine, dry over $Na_2SO_4$, filter, and evaporate in vacuo to give the title compound.

1.2 Synthesis of 6,6-dimethoxy-4-phenylhexanoic acid

Combine 1-trimethylsilyloxy-4-phenylcyclohex-1-ene from Example 1.1.2 (about 24.6 g, 100 mmol) and dichloromethane (200 mL) and methanol (300 mL). Cool in a dry-ice/acetone bath. Bubble with ozone until a blue color persists. After 5 minutes, purge with argon. After 20 minutes add dimethyl sulfide (40 mL, 540 mmol). After 16 hour, evaporate in vacuo to give a residue. Combine the residue, trimethylorthoformate (50 mL, 460 mmol), and acetyl chloride (10 mL, 200 mmol). Heat to reflux. After 4 hours, cool to ambient temperature and add potassium hydroxide (17 g, 300 mL) and water (200 mL). Heat to 60° C. After 1 hour, add an additional portion of potassium hydroxide (11.0 g, 200 mmol). After 1 additional hour, cool to ambient temperature. After 18 hours, evaporate in vacuo to leave an aqueous solution. Extract twice with methyl t-butyl ether. Cool the aqueous layer in an ice-bath and acidify using 1 M aqueous hydrochloric acid solution and extract with dichloromethane. Extract the organic layer with brine, dry over $Na_2SO_4$, filter, and evaporate in vacuo to give the title compound: $R_f$=0.26 (silica gel, 2/3 ethyl acetate/hexane).

1.3 Synthesis of (S)-4-benzyl-3-(6,6-dimethoxy-4-phenylhexanoyl)-2-oxazolidinone Combine 6,6-dimethoxy-4-phenylhexanoic acid (16.0 g, 63.4 mmol), triethylamine (10.6 mL, 76.1 mmol), and tetrahydrofuran (200 mL). Cool in a dry-ice/acetone bath. Add dropwise pivaloyl chloride (8.6 mL, 70 mmol). After 15 minutes, warm to 0° C. using an ice-bath. After 45 minutes, cool again in a dry-ice/acetone bath before adding, by cannula, a solution of litho (S)-4-benzyl-2-oxazolidinone, as prepared below. Combine (S)-4-benzyl-2-oxazolidinone (12.9 g, 73 mmol) and tetrahydrofuran (200 mL). Cool in a dry-ice acetone bath. Add dropwise a solution of n-butyl lithium (28.4 mL, 2.5 M, 71.0 mmol). After 1 hour, add, by cannula, to the mixed anhydride prepared above. After the addition is complete, warm slowly to ambient temperature. After 18 hours, quench the reaction mixture with water (5 mL) and partition between a saturated aqueous ammonium chloride solution and dichloromethane. Dry the organic layer over $Na_2SO_4$, filter, and evaporate in vacuo to give a residue. Chromatograph the residue on silica gel eluting sequentially with 1/4 ethyl acetate/hexane, 1/2 ethyl acetate/hexane, and then 2/3 ethyl acetate/hexane. Combine the product containing fractions, evaporate, and dry to give the title compound: $R_f$=0.43 (silica gel, 2/3 ethyl acetate/hexane).

1.4 Synthesis of (S)-4-benzyl-3-(2-azido-6,6-dimethoxy-4-phenylhexanoyl)-2-oxazolidinone Cool a solution of potassium hexamethyldisilazide (58 mL, 0.5 M in toluene, 29.0 mmol) in tetrahydrofuran in a dry-ice/acetone bath. Add dropwise a solution of (S)-4-benzyl-3-(6,6-dimethoxy-4-phenylhexanoyl)-2-oxazolidinone (10.6 g, 25.7 mmol) in tetrahydrofuran (100 mL). After 30 minutes, add a cold (−70°) solution of 2,4,6-triisopropylbenzenesulfonyl azide (9.9 g, 32 mmol) in tetrahydrofuran (50 mL). After 3 minutes, quench by the addition of acetic acid (6.9 mL, 120 mmol). After 5 minutes, warm to 35° C. After 1.5 hours, cool to ambient temperature, add water to dissolve salts, and evaporate in vacuo to give a residue. Partition the residue between a saturated aqueous ammonium chloride solution and ethyl acetate. Separate the layers, extract the organic layer with a saturated aqueous sodium bicarbonate solution, and then brine. Dry the organic layer over $Na_2SO_4$, filter, rinse with dichloromethane, and evaporate in vacuo to give a residue. Chromatograph the residue on silica gel eluting sequentially with 1/3 ethyl acetate/hexane, 1/2 ethyl acetate/hexane, and then 2/3 ethyl acetate/hexane. Combine the product containing fractions, evaporate, and dry to give the title compound: $R_f$=0.49 (silica gel, 2/3 ethyl acetate/hexane).

1.5 Synthesis of (S)-2-azido-6,6-dimethoxy-4-phenylhexanoic acid

Combine (S)-4-benzyl-3-(2-azido-6,6-dimethoxy-4-phenylhexanoyl)-2-oxazolidinone (9.6 g, 21.8 mmol) in tetrahydrofuran (300 mL), and water (90 mL). Cool in an ice bath. Add lithium hydroxide hydrate (1.05 g, 44 mmol) and an aqueous solution of hydrogen peroxide (8.75 mL, 30%, 77 mmol). After 3 hours, quench by the addition of a solution of sodium sulfite (12.0 g) in water (68 mL). Concentrate the quenched reaction mixture to remove most to the tetrahydrofuran and extract twice with diethyl ether. Cool the aqueous layer in an ice bath, acidify with an aqueous 6 M hydrochloric acid solution, and extract twice with dichloromethane. Dry the organic layer over $Na_2SO_4$, filter, and evaporate in vacuo to give the title compound: $R_f$=0.28 (silica gel, 5/95 methanol/dichloromethane).

1.6 Synthesis of 2-(trimethylsilyl)ethyl (S)-2-azido-6,6-dimethoxy-4-phenylhexanoate Combine (S)-2-azido-6,6-dimethoxy-4-phenylhexanoic acid (6.4 g, 21.8 mmol) and tetrahydrofuran (120 mL). Add 2-(trimethylsilyl)ethanol (9.4 mL, 66 mmol), pyridine (5.3 mL, 66 mmol), and 1-(3-dimethylaminopropyl)-3-ethylcarbodiimide hydrochloride (8.4 g, 44 mmol). After 2.5 days, evaporate in vacuo to give a residue. Partition the residue between methyl t-butyl ether (about 150 mL) and an aqueous 5% sulfuric acid solution. Separate the layers and extract the organic layer with a saturated aqueous sodium bicarbonate solution and then brine. Dry the organic layer over $Na_2SO_4$, filter, and evaporate in vacuo to give a residue. Chromatograph the residue on silica gel eluting sequentially with 1/7 ethyl acetate/hexane and then 1/6 ethyl acetate/hexane to give the title compound: $R_f$=0.51 (silica gel, 1/6 ethyl acetate/hexane).

1.7 Synthesis of 2-(trimethylsilyl)ethyl (S)-2-azido-6-oxo-4-phenylhexanoate

Combine 2-(trimethylsilyl)ethyl (S)-2-azido-6,6-dimethoxy-4-phenylhexanoate (3.0 g, 7.62 mmol), acetic acid (30 mL), tetrahydrofuran (10 mL), and water (10 mL). Heat to 60° C. After 4 hours, cool to ambient temperature and evaporate in vacuo to give a residue. Partition the residue between methyl t-butyl ether (about 125 mL) and brine (50 mL). Separate the layers, dry the organic layer over $Na_2SO_4$, filter, and evaporate in vacuo to give a residue. Chromatograph the residue on silica gel eluting with 1/6 ethyl acetate/hexane to give the title compound: $R_f$=0.36 (silica gel, 1/6 ethyl acetate/hexane).

1.8 Synthesis of 2-(trimethylsilyl)ethyl (S)-2-azido-6-((S)-t-butyl phenylalanyl)-4-phenylhexanoate Combine 2-(trimethylsilyl)ethyl (S)-2-azido-6-oxo-4-phenylhexanoate (0.72 g, 2.06 mmol), t-butyl (S)-phenylalanine hydrochloric acid salt (1.59 g, 6.2 mmol) and methanol (20 mL). Add powdered 3 Å molecular sieves (about 1.4 g). After 30 minutes add a solution of sodium cyanoborohydride (0.73 mL, 1.0 M in tetrahydrofuran, 0.73 mmol). After 2.5 hours, filter through celite and evaporate in vacuo to give a residue. Combine the residue and dichloromethane, extract with a saturate sodium bicarbonate solution and then brine, dry the organic layer over $Na_2SO_4$, filter, and evaporate in vacuo to give the title compound.

1.9 Synthesis of (S)-2-azido-6-((S)-t-butyl phenylalanyl)-4-phenylhexanoic acid

Combine 2-(trimethylsilyl)ethyl (S)-2-azido-6-((S)-t-butyl phenylalanyl)-4-phenylhexanoate (0.80 g, 1.45 mmol) and tetrahydrofuran (15 mL). Add a solution of tetrabutyl ammonium fluoride (2.2 mL, 1.0 M in tetrahydrofuran, 2.2 mmol). After 3 hours, evaporate in vacuo to give a residue. Partition the residue between ethyl acetate and an aqueous 1M hydrochloric acid solution. Separate the layers and extract the organic layer with brine, dry over $Na_2SO_4$, filter, and evaporate in vacuo to give the title compound.

1.10 Synthesis of N-[hexahydro-1-[1-(phenylmethyl)-1-t-butoxycarbonylmethyl]-2-oxo-3-azido-5-phenyl-1H-azepin]

Combine (S)-2-azido-6-((S)-t-butyl phenylalanyl)-4-phenylhexanoic acid (0.65 g, 1.45 mmol) and tetrahydrofuran (27 mL). Cool in an ice bath. Add N-methylmorpholine (0.35 mL, 3.2 mmol) and then isobutyl chloroformate (0.24 mL, 1.85 mmol). After 2.5 hours, filter, rinse solids with tetrahydrofuran, and concentrate in vacuo, filter through a short column of silica gel eluting with 2/1 ethyl acetate/hexane. Evaporate to give the title compound.

1.11 Synthesis of N-[hexahydro-1-[1-(phenylmethyl)-1-t-butoxycarbonylmethyl]-2-oxo-3-amino-5-phenyl-1H-azepin]

Combine N-[hexahydro-1-[1-(phenylmethyl)-1-t-butoxycarbonylmethyl]-2-oxo-3-azido-5-phenyl-1H-azepin] (0.32 g, 0.74 mmol) and methanol (12 mL). Degas by three cycles of evacuation and filling with nitrogen gas. Add 1,3-propanedithiol (0.40 mL, 4.0 mmol) and triethylamine (0.54 mL, 3.9 mmol). After 42 hours, evaporate in vacuo to give the title compound.

1.12 Synthesis of N-[hexahydro-1-[1-(phenylmethyl)-1-t-butoxycarbonylmethyl]-2-oxo-5-phenyl-1H-azepin-3-yl]-1,3-dihydro-a-bromo-1,3-dioxo-2H-isoindole-2-hexanamide Combine N-[hexahydro-1-[1-(phenylmethyl)-1-t-butoxycarbonylmethyl]-2-oxo-3-amino-5-phenyl-1H-azepin] (0.14 g, 0.34 mmol), 2-bromo-6-phthalimidohexanoic acid (0.189 g, 0.56 mmol), 1-(3-dimethylaminopropyl)-3-ethylcarbodiimide hydrochloride (0.106 g, 0.55 mmol), and 1-hydroxybenztriazole hydrate (75 mg, 0.56 mmol) in dichloromethane (8 mL). After 17 hours, evaporate in vacuo to give a residue, partition the residue between ethyl acetate and an aqueous 5% sulfuric acid solution (about 20 mL). Separate the layers, extract the organic layer with a saturate aqueous sodium bicarbonate solution and then brine, dry over $Na_2SO_4$, filter, and evaporate in vacuo to give the title compound.

1.13 Synthesis of N-[hexahydro-1-[1-(phenylmethyl)-1-t-butoxycarbonylmethyl]-2-oxo-5-phenyl-1H-azepin-3-yl]-1,3-dihydro-a-(p-methoxybenzylthio)-1,3-dioxo-2H-isoindole-2-hexanamide Combine p-methoxybenzylmercaptan (0.08 mL, 0.57 mmol) and sodium hydride (17 mg, 60% oil dispersion, 0.42 mmol) in degassed dimethylformamide (3 mL). After 1 hour, tetra-n-butylammonium iodide (about 5 mg) and N-[hexahydro-1-[1-(phenylmethyl)-1-t-butoxycarbonylmethyl]-2-oxo-5-phenyl-1H-azepin-3-yl]-1,3-dihydro-a-bromo-1,3-dioxo-2H-isoindole-2-hexanamide (0.20 g, 0.27 mmol). After 20 hours, quench be the addition of a saturated aqueous ammonium chloride solution and dilute with water (about 5 mL). Extract with ethyl acetate (about 75 mL). Separate the layers and extract the organic layer with brine, dry over $Na_2SO_4$, filter, and evaporate in vacuo to give the title compound.

1.14 Synthesis of N-[hexahydro-1-[1-(phenylmethyl)-1-carboxymethyl]-2-oxo-5-phenyl-1H-azepin-3-yl]-1,3-dihydro-α-mercapto-1,3-dioxo-2H-isoindole-2-hexanamide Combine N-[hexahydro-1-[1-(phenylmethyl)-1-t-butoxycarbonylmethyl]-2-oxo-5-phenyl-1H-azepin-3-yl]-1,3-dihydro-a-(p-methoxybenzylthio)-1,3-dioxo-2H-isoindole-2-hexanamide (0.16 g, 0.20 mmol), mercury (II)

acetate (0.084 g, 0.26 mmol), and anisole (0.23 mL, 2.1 mmol) in dichloromethane (6.6 mL). Cool in an ice bath and degas by repeatedly cycles of vacuum and filling the vessel with nitrogen gas. Add trifluoroacetic acid (2.5 mL). After 1 hour, warm to ambient temperature. After 3 hours, purge with hydrogen sulfide (gas) for about 10 minutes. Filter and evaporate in vacuo to give a residue. Repeatedly, combine the residue and carbon tetrachloride and evaporate in vacuo to give the title compound.

EXAMPLE 2

N-[Hexahydro-1-[1-(phenylmethyl)-1-carboxymethyl]-2-oxo-5-methyl-1H-azepin-3-yl]-1,3-dihydro-α-mercapto-1,3-dioxo-2H-isoindole-2-hexanamide

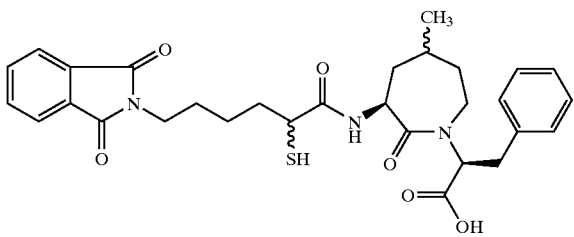

Synthesis of N-[hexahydro-1-[1-(phenylmethyl)-1-carboxymethyl]-2-oxo-5-methyl-1H-azepin-3-yl]-1,3-dihydro-α-mercapto-1,3-dioxo-2H-isoindole-2-hexanamide Prepare by the methods of Example 1.1–1.14 using 4-methylcyclohexane to give the title compound.

EXAMPLE 3

N-[Hexahydro-1-[1-(phenylmethyl)-1-carboxymethyl]-2-oxo-5-phenyl-1H-azepin-3-yl]-α-mercapto-3-phenylpropionamide

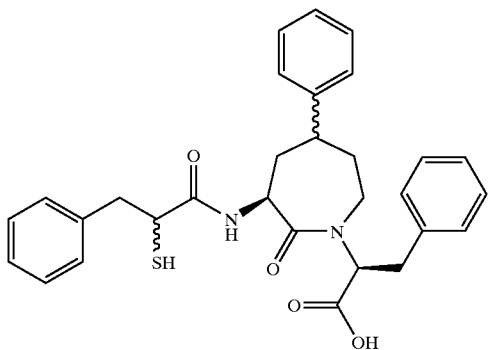

Synthesis of N-[hexahydro-1-[1-(phenylmethyl)-1-carboxymethyl]-2-oxo-5-phenyl-1H-azepin-3-yl]-α-mercapto-3-phenylpropionamide Prepare by the methods of Preparation 1 using 3-phenylpropionic acid or a-bromo-3-phenylpropionic acid as prepared in U.S. Pat. No. 5,491,143, issued Feb. 13, 1996 and Example 1.12–1.14 to give the title compound.

In a further embodiment, the present invention provides a method of inhibiting matrix metalloproteinase (MMP) to a patient in need thereof comprising administering to the patient an effective matrix metalloproteinase inhibiting amount of a compound of formula (1).

As used herein, the term "patient" refers to warm-blooded animals or marnmmals, including guinea pigs, dogs, cats, rats, mice, hamsters, rabbits and primates, including humans. A patient is in need of treatment to inhibit MMP when it would be beneficial to the patient to reduce the physiological effect of active MMP. For example, a patient is in need of treatment to inhibit MMP when a patient is suffering from a disease state characterized by excessive tissue disruption or tissue degradation, such as, but not limited to, a neoplastic disease state or cancer; rheumatoid arthritis; osteoarthritis; chronic inflammatory disorders, such as emphysema or chronic bronchitis; cardiovascular disorders, such as atherosclerosis; corneal ulceration; dental diseases, such as gingivitis or periodontal disease; and neurological disorders, such as multiple sclerosis.

The identification of those patients who are in need of treatment to inhibit MMP is well within the ability and knowledge of one skilled in the art. A clinician skilled in the art can readily identify, by the use of clinical tests, physical examination and medical/family history, those patients who are suffering from disease states characterized by excessive tissue disruption or tissue degradation.

An "effective matrix metalloproteinase inhibiting amount" of a compound of formula (1) is an amount which is effective, upon single or multiple dose administration to the patient, in providing relief of symptoms associated with MMP and is thus effective in inhibiting MMP-induced tissue disruption and/or MMP-induced tissue degradation. As used herein, "relief of symptoms" of MMP-mediated conditions refers to decrease in severity over that expected in the absence of treatment and does not necessarily indicate a total elimination or cure of the disease. Relief of symptoms is also intended to include prophylaxis.

An effective matrix metalloproteinase inhibiting dose can be readily determined by the use of conventional techniques and by observing results obtained under analogous circumstances. In determining the effective dose, a number of factors are considered including, but not limited to: the species of the patient; its size, age, and general health; the specific disease involved; the degree of involvement or the severity of the disease; the response of the individual patient; the particular compound administered; the mode of administration; the bioavailability characteristics of the preparation administered; the dose regimen selected; and the use of concomitant medication.

An effective matrix metalloproteinase inhibiting amount of a compound of formula (1) will generally vary from about 0.1 milligram per kilogram of body weight per day (mg/kg/day) to about 300 milligrams per kilogram of body weight per day (mg/kg/day). A daily dose of from about 1 mg/kg to about 100 mg/kg is preferred.

The term "neoplastic disease state" as used herein refers to an abnormal state or condition characterized by rapidly proliferating cell growth or neoplasm. Neoplastic disease states for which treatment with a compound of formula (1) will be particularly useful include: Leukemias, such as, but not limited to, acute lymphoblastic, chronic lymphocytic, acute myeloblastic and chronic myelocytic; Carcinomas and adenocarcinomas, such as, but not limited to, those of the cervix, oesophagus, stomach, small intestines, colon, lungs (both small and large cell), breast and prostate; Sarcomas, such as, but not limited to, oesteroma, osteosarcoma, lipoma, liposarcoma, hemangioma and hemangiosarcoma; Melanomas, including amelanotic and melanotic; and mixed types of neoplasias such as, but not limited to carcinosarcoma, lymphoid tissue type, follicullar reticulum, cell sarcoma and Hodgkin's Disease. Neoplastic disease states for which treatment with a compound of formula (1) will be particularly preferred include carcinomas and adenocarcinomas, particularly of the breast, prostate and lung.

Atherosclerosis is a disease state characterized by the development and growth of atherosclerotic lesions or plaque. The identification of those patients who are in need of treatment for atherosclerosis is well within the ability and knowledge of one of ordinary skill in the art. For example, individuals who are either suffering from clinically significant atherosclerosis or who are at risk of developing clinically significant atherosclerosis are patients in need of treatment for atherosclerosis. A clinician of ordinary skill in the art can readily determine, by the use of clinical tests, physical examination and medical/family history, if an individual is a patient in need of treatment for atherosclerosis.

The term "chronic inflammatory disease" refers to diseases or conditions characterized by persistent inflammation in the absence of an identifiable irritant or microbial pathogen. Inflammatory diseases for which treatment with a compound of formula (1) will be particularly useful include: emphysema, chronic bronchitis, asthma, and chronic inflammation, and especially smoking-induced emphysema.

In effecting treatment of a patient, a compound of formula (1) can be administered in any form or mode which makes the compound bioavailable in effective amounts, including oral and parenteral routes. For example, the compound can be administered orally, subcutaneously, intramuscularly, intravenously, transdermally, topically, intranasally, rectally, and the like. Oral administration is generally preferred. One skilled in the art of preparing formulations can readily select the proper form and mode of administration depending upon the disease state to be treated, the stage of the disease, and other relevant circumstances. Remington's Pharmaceutical Sciences, 18th Edition, Mack Publishing Co. (1990).

A compound of formula (1) can be administered in the form of pharmaceutical compositions or medicaments which are made by combining a compound of formula (1) with pharmaceutically acceptable carriers or excipients, the proportion and nature of which are determined by the chosen route of administration, and standard pharmaceutical practice.

The pharmaceutical compositions or medicaments are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, gels, ointments, aerosol or the like.

The pharmaceutical compositions may be administered orally, for example, with an inert diluent or with an edible carrier. They may be enclosed in gelatin capsules or compressed into tablets. For the purpose of oral therapeutic administration, a compound of formula (1) may be incorporated with excipients and used in the form of tablets, troches, capsules, elixirs, suspensions, syrups, wafers, chewing gums and the like. These preparations should contain at least 4% of a compound of formula (1), the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more of the following adjuvants: binders, such as microcrystalline cellulose, gum tragacanth or gelatin; excipients, such as starch or lactose, disintegrating agents such as alginic acid, Primogel, corn starch and the like; lubricants, such as magnesium stearate or Sterotex; glidants, such as colloidal silicon dioxide; and sweetening agents, such as sucrose or saccharin may be added or flavoring agents, such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, sucrose as a sweetening agent and certain preservatives, dyes and colorings and flavors. Materials used in preparing these various compositions should be pharmaceutically pure and non-toxic in the amounts used.

For the purpose of parenteral administration, a compound of formula (1) may be incorporated into a solution or suspension. These preparations should contain at least 0.1% of a compound of the invention, but may be varied to be between 0.1 and about 50% of the weight thereof. The amount of the active ingredient present in such compositions is such that a suitable dosage will be obtained.

The solutions or suspensions may also include one or more of the following adjuvants depending on the solubility and other properties of a compound of formula (1): sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

The MMP inhibitors of the present invention can be evaluated by the procedures that follow.

EXAMPLE A

Source and Activation of pro MMP-1

ProMMP-1 (EC 3.4.24.7; interstitial collagenase) was purified from culture medium of human rheumatoid synovial fibroblasts stimulated with macrophage-conditioned medium according to Okada, Y. et al., *J. Biol. Chem.* 261, 14245–14255 (1986). The active MMP-1 was obtained by treatment of proMMP-1 with trypsin (5 $\mu$g/mL) at 37° C. for 30 minutes, followed by addition of soybean trypsin inhibitor (50 $\mu$g/mL).

Determination of Inhibition Constant ($K_i$) for MMP-1

The activated MMP-1 is assayed using a fluorogenic substrate, Mca-Pro-Leu-Gly-Leu-Dpa-Ala-Arg-NH$_2$, Knight, C. G. et al., *FEBS Lett.* 296, 263–266 (1992), at 37° C. in 2.0 mL of assay buffer containing 50 mM Tris, pH 7.6, 0.2 M sodium chloride, 50 mM calcium chloride, and 0.02% Brij-35. The increase in fluorescence due to cleavage of Gly-Leu peptide bond by MMP-3 was monitored with Perkin-Elmer LS50B Fluorimeter ($\lambda_{ex}$ 328 nm, $\lambda_{em}$ 393 nm, excitation slit 2.5, emission slit 10). Substrate and inhibitor stock solutions were made in DMF. For determination of $K_i$ values for MMP-1 inhibitors, a series of intermediate inhibitor solutions were prepared in DMF and 1 or 2 $\mu$L of the diluted inhibitor solution was mixed with 1 $\mu$L of 2 mM substrate solution in DMF in a quartz cuvette containing 2 mL of assay buffer. The enzyme (10 $\mu$L of 0.2 $\mu$M MMP-3 dilution in assay buffer) was added at the last to start the reaction. For routine measurement of a $K_i$ value for a reversible, competitive inhibitor, the initial rates in the presence of at least four inhibitor concentrations (two concentrations above $K_i$ and two concentrations below $K_i$) were measured using [S]=1 μM (<<$K_m$) and [MMP-1]=0.8 nM. Under these conditions, the measured $K_{i,\ app}$ is close to true $K_i$.

Calculation of $K_i$ Values

The $K_i$ for a competitive inhibitor is calculated using: $v_0/v_i=(1+[I]/K_{i,\ app})$ and $K_i=K_{i,\ app}/(1+[S]/K_m)$, where $v_0$ is the initial rate in the absence of inhibitor, $v_i$ is the initial rate in the presence of inhibitor at the concentration of [I], [S] is the substrate concentration, and $K_m$ is the Michaelis constant. If slow binding is observed (i.e. if the approach to the binding equilibrium is slow), the final steady-state rate rather than the initial rate is taken as $v_i$.

EXAMPLE B

Source and Activation of proMMP-2

Recombinant MMP-2 was purified from the fermentation broth of yeast *Pichia pastoris* that carries the integrated MMP-2 gene into its chromosome. In brief, the full-length cDNA for MMP-2 was obtained by reverse transcription of RNA from human melanoma A375M cell line by the reverse transcriptase polymerase chain reaction (RT-PCR) using sequence specific oligonucleotides. The nucleotide sequence was confirmed by Taq cycle sequencing. The cDNA was ligated into the *Pichia pastoris* expression vector pHIL-D2 in such a way that the expression of pro-MMP-2 is under the control of the methanol inducible alcohol oxidase promoter. The expression construct was digested with either SalI or NsiI and used to transform the *Pichia pastoris* strains KM71 and SMD1168. A large-scale culture of a selected clone designated 24S was performed in a high cell density fermentor and the recombinant MMP-2 was purified from the culture supernatant by gelatin-sepharose 4B (Pharmacia). The enzyme is sufficiently pure at this stage for routine measurement of inhibition. If desired, however, the enzyme may be further purified by AcA 44 gel filtration (Spectra).

Determination of Inhibition Constant ($K_i$) for MMP-2

The active MMP-2 was obtained by activation of proMMP-2 at 37° C. for 1 h with 4-aminophenylmercuric acetate which was then removed by a Sephadex G-50 spin column. The enzyme is assayed using a fluorogenic substrate, Mca-Pro-Leu-Gly-Leu-Dpa-Ala-Arg-NH$_2$, at 37° C. in 2.0 mL of assay buffer containing 50 mM Tris, pH 7.6, 0.2 M sodium chloride, 50 mM calcium chloride, 0.02% Brij-35, and 50 μM β-mercaptoethanol. The increase in fluorescence is monitored ($\lambda_{ex}$ 328 nm, $\lambda_{em}$ 393 nm). Substrate and inhibitor stock solutions are made in DMF. The enzyme is added at the last to start the reaction. For routine measurement of a $K_i$ value for a reversible, competitive inhibitor, the initial rates in the presence of at least four inhibitor concentrations (two inhibitor concentrations above $K_i$ and two below $K_i$) are measured using [S]=1 μM (<<$K_m$) and [MMP-2]=0.4 nM. Under these conditions, the measured $K_{i,\ app}$ is close to true $K_i$.

EXAMPLE C

Source and Activation of proMMP-3

ProMMP-3 (EC 3.4.24.17; Stromelysin-1) was purified from culture medium of human rheumatoid synovial fibroblasts stimulated with macrophage-conditioned medium according to Okada, Y. et al., *J. Biol. Chem.* 261, 14245–14255 (1986). The active MMP-3 was obtained by treatment of proMMP-3 with trypsin (5 μg/mL) at 37° C. for 30 minutes, followed by addition of soybean trypsin inhibitor (50 μg/mL). Aliquots of the activated MMP-3 were stored at −20° C.

Determination of Inhibition Constant ($K_i$) for MMP-3

The activated MMP-3 is assayed using a fluorogenic substrate, Mca-Pro-Leu-Gly-Leu-Dpa-Ala-Arg-NH$_2$, Knight, C. G. et al., *FEBS Lett.* 296, 263–266 (1992), at 37° C. in an assay buffer containing 50 mM Tris, pH 7.6, 0.2 M sodium chloride, 50 mM calcium chloride, and 0.02% Brij-35. The increase in fluorescence due to cleavage of Gly-Leu peptide bond by MMP-3 was monitored with Perkin-Elmer LS50B Fluorimeter ($\lambda_{ex}$ 328 nm, $\lambda_{em}$ 393 nm, excitation slit 2.5, emission slit 10). Substrate and inhibitor stock solutions were made in DMF and 0.1% HCl-DMF, respectively. For determination of $K_i$ values for MMP-3 inhibitors, a series of intermediate inhibitor solutions were prepared in 0.1% HCl-DMF and 1 or 2 μL of the diluted inhibitor solution was mixed with 1 μL of 2 mM substrate solution in DMF in a quartz cuvette containing 2 mL of assay buffer. The enzyme (10 μL of 0.2 μM MMP-3 dilution in assay buffer) was added at the last to start the reaction. For routine measurement of a $K_i$ value for a reversible, competitive inhibitor, the initial rates in the presence of at least four inhibitor concentrations (two concentrations above $K_i$ and two concentrations below $K_i$) were measured using [S]=1 μM (<<$K_m$) and [MMP-3]=1 nM. Under these conditions, the measured $K_{i,\ app}$ is close to true $K_i$.

Calculation of $K_i$ Values

The $K_i$ for a competitive inhibitor is calculated using: $v_0/v_i=(1+[I]/K_{i,\ app})$ and $K_i=K_{i,\ app}/(1+[S]/K_m)$, where $v_0$ is the initial rate in the absence of inhibitor, $v_i$ is the initial rate in the presence of inhibitor at the concentration of [I], [S] is the substrate concentration, and $K_m$ is the Michaelis constant. If slow binding is observed (i.e. if the approach to the binding equilibrium is slow), the final steady-state rate rather than the initial rate is taken as $v_i$.

EXAMPLE D

Source of MMP-12 (Macrophage Metalloelastase)

MMP-12 (EC 3.4.24.65) was cloned, expressed and purified according to Shapiro, S. D. et al., *J Biol. Chem.* 268, 23824–23829 (1993). Autoactivation resulted in the fully processed active form of the enzyme. Aliquots of MMP-12 were stored at −70° C.

Determination of the Inhibition Constant ($K_i$) for MMP-12.

The potency of inhibitors of MMP-12 was measured using either quartz cuvettes or microtiter plates. The activity of MMP-12 was measured using a fluorogenic substrate, Mca-Pro-Leu-Gly-Leu-Dpa-Ala-Arg-NH$_2$, Knight, C. G. et al., *FEBS Lett.* 296, 263–266 (1992), at 25° C. in an assay buffer containing 50 mM Tris, pH 7.6, 0.2 M sodium chloride, 50 mM calcium chloride, and 0.02% Brij-35. The increase in fluorescence due to cleavage of Gly-Leu peptide bond by MMP-12 was monitored with a Perkin-Elmer LS50B Fluorimeter ($\lambda_{ex}$ 328 nm, $\lambda_{em}$ 393 nm, excitation slit 2.5, emission slit 10) for the cuvette assay and with a Molecular Devices Fmax fluorescence plate reader ($\lambda_{ex}$ 320 nm, $\lambda_{em}$ 405 nm) for the microtiter plate assay. Substrate and inhibitor stock solutions were made in N,N-dimethylformamide (DMF) and 0.1% HCl-DMF, respectively.

$K_i$ values were determined using the cuvette method by preparing a series of intermediate inhibitors solutions in 0.1% HCl-DMF and mixing the inhibitor with substrate (final concentration 2 μM) in a quartz cuvette containing 2 ml of assay buffer. MMP-12 was added to start the reaction at a concentration of 2 nM and progress curves were generated. For routine measurement of a $K_i$ value for a reversible competitive inhibitor, the initial rates in the presence of at least four inhibitor concentrations (two concentrations above and two concentrations below the $K_i$) were measured [S]=2 μM (<<$K_m$) and [MMP-12]=2 nM. Under these conditions, the measured $K_{i,app}$ is close to the true $K_i$.

$K_i$ values were determined using the microtiter plate method in a manner similar to that described for the cuvette method with some modifications. Four different inhibitor concentrations (50 µl in assay buffer)of each compound were added to separate wells of a microtiter plate and substrate was added (100 µl) to get a final concentration of 4 mM. MMP-12 was added to a final concentration of 2 nM (50 µl) to start the reaction. Cleavage of substrate was recorded every 30 seconds for 30 minutes and progress curves were generated.

Calculation of $K_i$ Values

The Ki for a competitive inhibitor was calculated using: $V_0/V_i=(1+[I]/K_{i,app})$ and $K_i=K_{i,app}/(1+[S]/K_m)$, where $V_0$ is the initial rate in the absence of inhibitor, $V_i$ is the initial rate in the presence of inhibitor at the concentration of [I], [S] is the substrate concentration, and $K_m$ is the Michaelis constant. If slow binding is observed (i.e. if the approach to the binding equilibrium is slow), the final steady-state rate rather than the initial rate is taken as $V_i$.

What is claimed is:

1. A compound of the formula wherein
  $R_1$ is selected from a group consisting of hydrogen, $C_1-C_6$ alkyl, —CH$_2$SCH$_2$NHCOCH$_3$, —(CH$_2$)$_p$—A, —(CH$_2$)$_m$—B, and —CH$_2$—D—R$_7$;
  wherein
    A is selected from a group consisting of $C_6-C_{10}$ aryl, $C_3-C_9$ heteroaryl, or cyclohexyl;
    B is selected from a group consisting of —N(R$_7$)$_2$, guanidino, nitroguanidino, —C(O)OR$_6$ and —C(O)NR$_6$;
    D is selected from a group consisting of oxy and thio;
  $R_2$ is selected from a group consisting of $C_1-C_4$ alkyl, —(CH$_2$)$_p$—(C$_3$–C$_9$) heteroaryl, and —(CH$_2$)$_p$—Ar$_1$;
  wherein
    Ar$_1$ is selected from the group consisting of phenyl and naphthyl optionally substituted with a substituent selected from the group consisting of halogen, $C_1-C_4$ alkyl, —OR$_6$, —N(R$_6$)$_2$, —SO$_2$N(R$_6$)$_2$ and —NO$_2$;
  $R_3$ is selected from a group consisting of W—(CH$_2$)$_m$—, and Q—Z—(CH$_2$)$_m$—;
  wherein
    W is phthalimido;
    Z is selected from the group consisting of —O—, —NR$_6$—, —C(O)NR$_6$—, —NR$_6$C(O)—, —NHC(O)NR$_6$—, —OC(O)NR$_6$—, —HNC(O)O—, and —SO$_2$NR$_6$—;
    Q is selected from the group consisting of hydrogen, and Y—(CH$_2$)$_n$—;
    wherein
      Y is selected from the group consisting of hydrogen, $C_6-C_{10}$ aryl, $C_3-C_9$ heteroaryl, —C(O)OR$_6$, —N(R$_6$)$_2$, morpholino, piperidino, pyrrolidino, and isoindolyl;
  $R_4$ is selected from a group consisting of hydrogen, —C(O)R$_7$, —C(O)—(CH$_2$)$_q$—K and —S—G;

wherein
  K is selected from the group consisting of

G is selected from the group consisting of $R_6$ is selected from the group consisting of hydrogen and $C_1-C_6$ alkyl;
  $R_7$ is selected from the group consisting of hydrogen, $C_1-C_4$ alkyl, and —(CH$_2$)$_p$—Ar$_2$;
  wherein
    Ar$_2$ is selected from the group consisting of phenyl and naphthyl optionally substituted with a substituent selected from the group consisting of halogen, $C_1-C_4$ alkyl, —OR$_6$, —N(R$_6$)$_2$, —SO$_2$N(R$_6$)$_2$ and —NO$_2$;
  $R_9$ and $R_{10}$ are each independently selected from the group consisting of $C_1-C_4$ alkyl and —(CH$_2$)$_p$—Ar$_2$;
  $R_{11}$ is selected from the group consisting of —CF$_3$, $C_1-C_{10}$ alkyl and —(CH$_2$)$_p$—Ar$_2$;
  $R_{12}$ is selected from the group consisting of hydrogen, $C_1-C_6$ alkyl, —CH$_2$CH$_2$S(O)$_p$CH$_3$, and arylalkyl;
  $R_{13}$ is selected from the group consisting of hydrogen, hydroxy, amino, $C_1-C_6$ alkyl, N-methylamino, N,N-dimethylamino, —CO$_2$R$_{17}$ and —OC(O)R$_{18}$;
  wherein
    $R_{17}$ is selected from the group consisting of hydrogen, —C(O)C(CH$_3$)$_3$, $C_1-C_4$ alkyl, —(CH$_2$)$_p$—Ar$_2$, and diphenylmethyl;
  $R_{18}$ is hydrogen, $C_1-C_6$ alkyl and phenyl;

$R_{14}$ is selected from the group consisting of 1 or 2 substituents independently chosen from the group consisting of hydrogen, $C_1$–$C_4$ alkyl, $C_1$–$C_4$ alkoxy, and halogen;

$R_{15}$ is selected from the group consisting of hydrogen, $C_1$–$C_6$ alkyl and —$(CH_2)_p$—$Ar_2$;

$R_{16}$ is selected from the group consisting of hydrogen and $C_1$–$C_4$ alkyl;

$V_1$ is selected from the group consisting of —O—, —S—, and —NH—;

$V_2$ is selected from the group consisting of —N— and —CH—;

$V_3$ is selected from the group consisting of a bond and —C(O)—;

$V_4$ is selected from the group consisting of —$(CH_2)_{w'}$—, —O—, —S—, —$NR_7$—, and —$NC(O)R_{11}$—;

X' is selected from the group consisting of —CH— and —N—;

m is an integer from 2–4;
n is an integer from 0–4;
p is an integer from 0–2;
t is an integer from 1–2;
w is an integer from 1–3;
w' is an integer from 0–1;

or a pharmaceutically acceptable salt, stereoisomer or hydrate thereof.

2. A compound of claim 1 wherein $R_1$ is a —$(CH_2)_p$—A group.

3. The compound of claim 2 wherein p is 1 or 2 and A is $C_6$ aryl.

4. A compound of claim 1 wherein $R_2$ is a —$(CH_2)_p$—$Ar_1$ group.

5. A compound of claim 4 wherein p is 0 and $Ar_1$ is phenyl or substituted phenyl.

6. A compound of claim 5 wherein $Ar_1$ is phenyl.

7. A compound of claim 1 wherein $R_3$ is a W—$(CH_2)_m$— group.

8. A compound of claim 1 wherein $R_3$ is $C_1$–$C_6$ alkyl.

9. A compound of claim 1 wherein $R_3$ is a Q—Z—$(CH_2)_m$— group.

10. A compound of any one of claims 1–9 wherein $R_4$ is hydrogen.

11. A compound of any one of claims 1–9 wherein $R_4$ is —$C(O)R_7$.

12. A compound of any one of claims 1–9 wherein $R_4$ a —S—G group.

13. A pharmaceutical composition comprising a compound of claim 1 and a pharmaceutically acceptable carrier.

14. A method of treating smoking-induced emphysema in a patient in need thereof which comprises administering to the patient an effective matrix metalloproteinase inhibiting amount of a compound of the formula

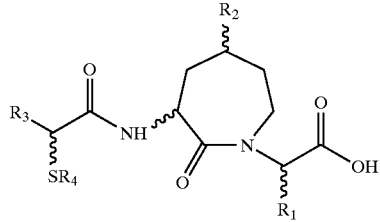

wherein $R_1$ is selected from a group consisting of hydrogen, $C_1$–$C_6$ alkyl, —$CH_2SCH_2NHCOCH_3$, —$(CH_2)_p$—A, —$(CH_2)_m$—B, and —$CH_2$—D—$R_7$;

wherein

A is selected from a group consisting of $C_6$–$C_{10}$ aryl, $C_3$–$C_9$ heteroaryl, or cyclohexyl;

B is selected from a group consisting of —$N(R_7)_2$, guanidino, nitroguanidino, —$C(O)OR_6$ and —$C(O)NR_6$;

D is selected from a group consisting of oxy and thio;

$R_2$ is selected from a group consisting of $C_1$–$C_4$ alkyl, —$(CH_2)_p$—$(C_3$–$C_9)$ hetetroaryl, and —$(CH_2)_p$—$Ar_1$;

wherein $Ar_1$ is selected from the group consisting of phenyl and naphthyl optionally substituted with a substituent selected from the group consisting of halogen, $C_1$–$C_4$ alkyl, —$OR_6$, —$N(R_6)_2$, —$SO_2N(R_6)_2$ and —$NO_2$, $R_3$ is selected from a group consisting of W—$(CH_2)_m$—, and Q—$Z(CH_2)_m$—;

wherein

W is phthalimido;

Z is selected from the group consisting of —O—, —$NR_6$—, —$C(O)NR_6$—, —$NR_6C(O)$—, —$NHC(O)NR_6$—, —$OC(O)NR_6$—, —$HNC(O)O$—, and —$SO_2NR_6$—;

Q is selected from the group consisting of hydrogen, and Y—$(CH_2)_n$—;

wherein

Y is selected from the group consisting of hydrogen, $C_6$–$C_{10}$ aryl, $C_3$–$C_9$ heteroaryl, —$C(O)OR_6$, —$N(R_6)_2$, morpholino, piperidino, pyrrolidino, and isoindolyl;

$R_4$ is selected from a group consisting of hydrogen, —$C(O)R_7$, —$C(O)$—$(CH_2)_q$—K and —S—G;

wherein

K is selected from the group consisting of

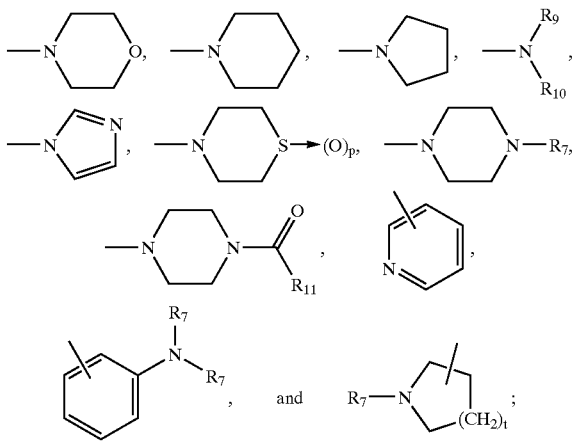

G is selected from the group consisting of

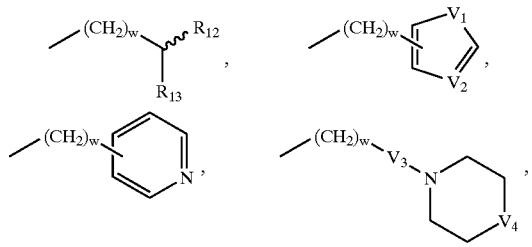

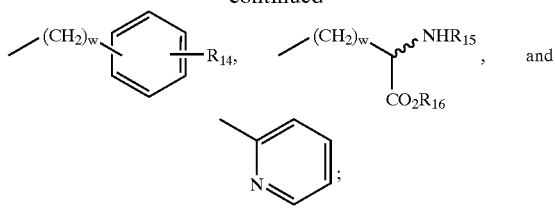

$R_6$ is selected from the group consisting of hydrogen and $C_1$–$C_6$ alkyl;

$R_7$ is selected from the group consisting of hydrogen, $C_1$–$C_4$ alkyl, and —$(CH_2)_p$—$Ar_2$;

wherein
  $Ar_2$ is selected from the group consisting of phenyl and naphthyl optionally substituted with a substituent selected from the group consisting of halogen, $C_1$–$C_4$ alkyl, —$OR_6$, —$N(R_6)_2$, —$SO_2N(R_6)_2$ and —$NO_2$;

$R_9$ and $R_{10}$ are each independently selected from the group consisting of $C_1$–$C_4$ alkyl and —$(CH_2)_p$—$Ar_2$;

$R_{11}$ is selected from the group consisting of —$CF_3$, $C_1$–$C_{10}$ alkyl and —$(CH_2)_p$—$Ar_2$;

$R_{12}$ is selected from the group consisting of hydrogen, $C_1$–$C_6$ alkyl, —$CH_2CH_2S(O)_pCH_3$, and arylalkyl;

$R_{13}$ is selected from the group consisting of hydrogen, hydroxy, amino, $C_1$–$C_6$ alkyl, N-methylamino, N,N-dimethylamino, —$CO_2R_{17}$ and —$OC(O)R_{18}$;

wherein
  $R_{17}$ is selected from the group consisting of hydrogen, —$C(O)C(CH_3)_3$, $C_1$–$C_4$ alkyl, $(CH_2)_p$—$Ar_2$, and diphenylmethyl;

$R_{18}$ is hydrogen, $C_1$–$C_6$ alkyl and phenyl;

$R_{14}$ is selected from the group consisting of 1 or 2 substituents independently chosen from the group consisting of hydrogen, $C_1$–$C_4$ alkyl, $C_1$–$C_4$ alkoxy, and halogen;

$R_{15}$ is selected from the group consisting of hydrogen, $C_1$–$C_6$ alkyl and —$(CH_2)_p$—$Ar_2$;

$R_{16}$ is selected from the group consisting of hydrogen and $C_1$–$C_4$ alkyl;

$V_1$ is selected from the group consisting of —O—, —S—, and —NH—;

$V_2$ is selected from the group consisting of —N— and —CH—;

$V_3$ is selected from the group consisting of a bond and —C(O)—;

$V_4$ is selected from the group consisting of —$(CH_2)_{w'}$—, —O—, —S—, —$NR_7$—, and —NC(O)$R_{11}$—;

X' is selected from the group consisting of —CH— and —N—;

m is an integer from 2–4;
n is an integer from 0–4;
p is an integer from 0–2;
t is an integer from 1–2;
w is an integer from 1–3;
w' is an integer from 0–1;

or a pharmaceutically acceptable salt, stereoisomer or hydrate thereof.

* * * * *